US007910337B2

(12) United States Patent
Haselbeck et al.

(10) Patent No.: US 7,910,337 B2
(45) Date of Patent: Mar. 22, 2011

(54) METHOD FOR IDENTIFYING DRUG-SENSITIZING ANTISENSE DNA FRAGMENTS AND USE THEREOF

(75) Inventors: Robert Haselbeck, San Diego, CA (US); Mark Hilgers, San Diego, CA (US); Karen Shaw, Poway, CA (US); Vickie Brown-Driver, Solana Beach, CA (US); Kedar Ge, San Diego, CA (US); John M. Finn, Encinitas, CA (US); Mark Stidham, San Diego, CA (US)

(73) Assignee: Trius Therapeutics, Inc., San Diego, CA (US)

( * ) Notice: Subject to any disclaimer, the term of this patent is extended or adjusted under 35 U.S.C. 154(b) by 837 days.

(21) Appl. No.: 11/636,394

(22) Filed: Dec. 8, 2006

(65) Prior Publication Data

US 2007/0218481 A1 Sep. 20, 2007

Related U.S. Application Data

(60) Provisional application No. 60/782,961, filed on Mar. 15, 2006.

(51) Int. Cl.
*C12P 19/34* (2006.01)
*C07H 21/04* (2006.01)
*C12N 15/63* (2006.01)
*C07K 16/00* (2006.01)
(52) U.S. Cl. .................. 435/91.2; 536/24.5; 435/320.1; 530/387.1
(58) Field of Classification Search .................. None
See application file for complete search history.

(56) References Cited

U.S. PATENT DOCUMENTS

2004/0029129 A1 2/2004 Wang et al. .................. 435/6

OTHER PUBLICATIONS

Read et al. (Nature 423, 81-86 (May 1, 2003).*
Blum et al., "Isolation of peptide aptamers that inhibit intracellular processes" *PNAS* 97:5, 2241-2246 (2000).
Ellington and Szostak, "In vitro selection of RNA molecules that bind specific ligands" *Nature*, 1990, 346:818-22.
Forsyth et al., "A genome-wide strategy for the identification of essential genes in *Staphylococcus aureus*", *Mol Microbiol*, 2002, 43(6):1387-400.
Hasan et al., "Antisense RNA does not significantly affect expression of the galK gene of *Escherichia coli* or the N gene of coliphage lambda" *Gene* 72:247-252 (1988).
Ji et al., "Identification of essential genes in *Staphylococcus aureus* using inducible antisense RNA", *Methods Enzymol*, 2002, 358:123-8.
Kernodle et al., "Expression of an Antisense hla Fragment in *Staphylococcus aureus* Reduces Alpha-Toxin Production In Vitro and Attenuates Lethal Activity in a Murine Model", *Infection and Immunity*, 1997, 65:179-184.
Lopes et al., "Transcriptional polarity enhances the contribution of the internal promoter, ilvEp, in the expression of the ilvGMEDA operon in wild-type *Escherichia coli* K12" *Mol Microbiol.*, Aug. 1989;3(8):1039-51.
Merino et al., "Antisense overlapping open reading frames in genes from bacteria to humans", *Nucleic Acids Res.*, 22:1903-1908, 1994.
Parish and Stoker, "Development and use of a conditional antisense mutagenesis system in mycobacterium" *FEMS Microbiology Letters* 154:151-157, 1997.
Pestka et al., "Anti-mRNA:Specific inhibition of translation of single mRNA molecules" *Proc. Natl. Acad. Sci. USA*, 1984, 81:7525-7528.
Spann et al., "Mutagenesis and gene identification in Dictyostelium by shotgun antisense", *Proc. Natl. Acad Sci.*, USA, 1996, 93:5003-5007.
Borrmann et al., "Short-Course Regimens of Artesunat-Fosmidomycin in Treatment of Uncomplicated *Plasmodium falciparum* Malaria", *Antimicrobial Agents and Chemotherapy*, 49(9):3749-3754 (2005).
Groom et al., "Trimethoprim Binds in a Bacterial Mode to the Wild-type and E30D Mutant of Mouse Dihydrofolate Reductase", *The Journal of Biological Chemistry*, 266(30):19890-19893 (1991).

* cited by examiner

*Primary Examiner* — Amy Bowman
(74) *Attorney, Agent, or Firm* — DLA Piper LLP (US)

(57) ABSTRACT

The invention provides a method for generating and selecting drug-sensitizing antisense DNA fragments. In one embodiment, the method includes identifying a gene of interest using knowledge of bacterial physiology, biochemistry, genetics, genomics, and other means. The method includes PCR amplification of a gene of interest using genomic DNA as a template; fragmentation of the DNA by sonication or other means; selecting DNA fragments no longer than 400 base pairs; ligating the DNA fragments into a suitable expression plasmid with a selectable marker; transforming the plasmids containing the DNA fragments into the organism from which the gene of interest originated; and selecting clones from transformed cells that show a phenotypic difference of the clone grown in the presence of the inducer relative to the phenotype in the absence of inducer.

48 Claims, 19 Drawing Sheets

Selection of gene target based on knowledge other than genomic antisense survey

Isolation of gene of interest and sheer into fragments < 200 base pairs

Clone into vector with inducible promoter

Tranform into bacteria and select transformants

Select clones growth inhibited in the presence of inducer

Validate clones with specific antisense activity and selective small molecule hypersensitivity

FIG. 2

Characterize inducer-dependence of growth attenuation

Select clones that have inducer-dependent reductions in mRNA for antisense target

Determine a Selective Inducer Concentration (SIC) that allows antisense expression but does not effect IC50 of organism to off-target antibiotics.

Determine IC50 sensitivities in the presence and absence of SIC to a panel of antibiotics and specific inhibitors.

Select clones selectively hypersensitive to on-target compounds.

FIG. 3

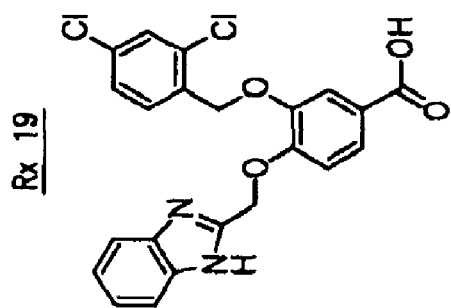
Rx 19
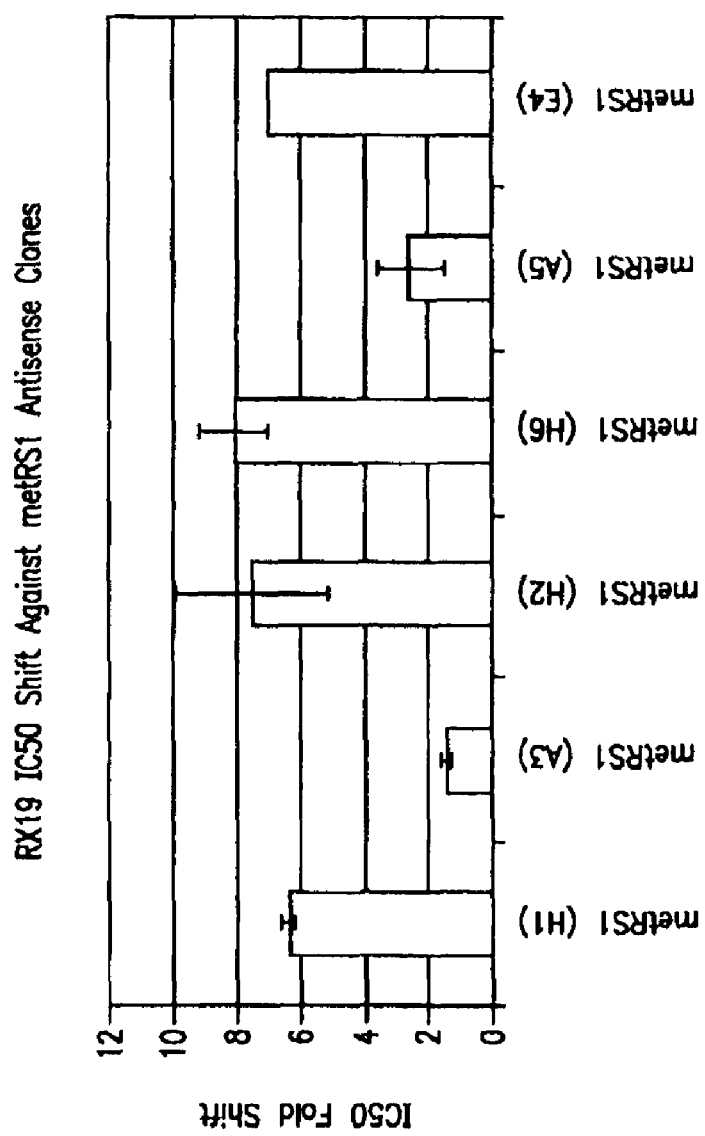
FIG. 4B

| SEQ ID | SOURCE ORGANISM | SEQUENCE |
|---|---|---|
| Ba-murB2-C1 | Bacillus anthracis | CCGCCAACTGAACCTGGAATACCACAAGCGAACTCAAGACCCGTTAAGTTATGGTCTAACGCAATACGTGATACGTCAATAATTGCTGCACCGCACTGTGCTACAATTGTCGT |
| Ba-murB2-H1 | Bacillus anthracis | CTCTTCAACTGTTTTTTGTACGAAGTGAATTAAATCGATGTAATCTTGTGCTGTTCCGTTATCAACATTTACCATAAATCCAGCGTGTTTTAAAGAAACGGATCGAATGTCATTATTAAAGACG |
| Ba-murB2-D1 | Bacillus anthracis | TGCATTCATATATAATGCTCCGCCAACTGAACCTGGAATACCACAAGCGAACTCAAGACCCGTTAAGTTATGGTCTAACGCAATACGTGATACGTCAATAATTGCTGCACCGCACTGTGCTACAATTGTCGTTCCTGTTACAGTAACACCTGTAATATGAATTAAACTTACTGT |
| Ba-murB2-D2 | Bacillus anthracis | AAGTTATGGTCTAACGCAATACGTGATACGTCAATAATTGCTGCACCGCACTGTGCTACAATTGTCGTTCCTGTTACAGTAACACCTGTAATATGAATTAAACTTACTGTAATCCCGCGAATTCCACCGTCTTTAATAATGACAT |
| Ba-metRS1-H1 | Bacillus anthracis | AATATAACTGGATCTACTACATTTCCTTTTGACTTACTCATCTTTCCATCCTTCATTAAAATCCAACCGTGAGCAAAGACTTTTTTCGGAAGAGGT |
| Ba-metRS1-H2 | Bacillus anthracis | AACTTATCTGCCTTTTTTACAGGTTCAGCAGATAGTACTTCAGCTACACGCAATTCTACTTTAAAGAAATCATCAATTGTAATTTCTTCTGCCTTCGGTCCTTCTTC |
| Ba-metRS1-H6 | Bacillus anthracis | ATCCTTCATTAAAATCCAACCGTGAGCAAAGACTTTTTTCGGAAGAGGTAAATCTAATGCCATTAAAATGATTGGCCAATAAATTGTATGGAAACGAACGATT |
| Ba-metRS1-E4 | Bacillus anthracis | GGTTGTCCTTTTTCTACTTTTGTTCCAGCTGGAATACAGCCGATTGTAGATAGGCTTCCCCAAGATGTATGTGCTTCATCAGTAAGGCCAAGC |
| Ba-uppS-UG9 | Bacillus anthracis | TTTAACGCGAAATTAAGAATTAATCCCGTATTCTCTTTCGTTTCTTCCATGGCCTTCTCCATCGCTCTGCGTGTATGCGTAGGAAGACGATCTTGTTGC |
| Ba-uppS-UA3 | Bacillus anthracis | CCTCTCTTTCTACACGCCTCCGAATCTGCGCCCTCTATGTTGAAAGTCTGT |
| Ba-dfrA-2G1 | Bacillus anthracis | CCAGGCAGTGGTCTACCAATCGCTTCATAGTTTTTTCTTCCCATAATAAGCGGGTGACCCATCGTTGTTTTCTTTACATACTGCAATTCACTCGGTAAACGCC |
| Ba-dfrA-2G6 | Bacillus anthracis | CAGGCAGTGGTCTACCAATCGCTTCATAGTTTTTTCTTCCCATAATAAGCGGGTGACCCATCGTTGTTTCTTTACATACTGCAATTCACTCGGTAAACGCCAAGGT |
| Sa-murB-E9 | Staphylococcus aureus | CCACCTTCACGGATAATAATATTTGAGCCATTTCCTAAATATGTAACAGGAATCTCATTTTGATAGGCATATTTAACAACTGCTTGTACTTCTTCATTTTTAGTAGGGGTAATGTAAAAGTCGGCATTACCACCTGTTTTAGTATAAGTGTATCGTTTTAAAGGTTCATCAACTTTAATTTTTTCATTTGGGATAAGT |
| Sa-murB-F7 | Staphylococcus aureus | CTTGCAAATTAGAATCTTGTATCAATTTACCTGCAAAATGACCAGGCGGTCTTTGGAATACACTACCACATGAAGGATACTCTAAAGGTTGTTTAGATTCTCTACGTTCTGTTAAATCATCCATTTTAGCTTGTATTTCAGTCATTTTACCAGGAGCTAAAGTAAATGC |
| Sa-murB-B9 | Staphylococcus aureus | ACCAATTGAACCTGGAATACCACATGCAAATTCAAGGCCAGTAAGTGCGTAATCACGAGCAACACGTGAGACATCAATAATTGCAGCGCCGCTACCGGCTATTATCGCATCATCAGATACTTCGATATGATCTAGTGATAATAAAC |

FIG. 9

SEQUENCE LISTING

```
<160> NUMBER OF SEQ ID NOS: 15

<210> SEQ ID NO 1
<211> LENGTH: 113
<212> TYPE: DNA
<213> ORGANISM: Bacillus anthracis Ba-murB2-C1

<400> SEQUENCE: 1
ccgccaactg aacctggaat accacaagcg aactcaagac ccgttaagtt atggtctaac      60
gcaatacgtg atacgtcaat aattgctgca ccgcactgtg ctacaattgt cgt            113

<210> SEQ ID NO 2
<211> LENGTH: 124
<212> TYPE: DNA
<213> ORGANISM: Bacillus anthracis Ba-murB2-H1

<400> SEQUENCE: 2
ctcttcaact gttttttgta cgaagtgaat taaatcgatg taatcttgtg ctgttccgtt      60
atcaacattt accataaatc cagcgtgttt taaagaaacg gatcgaatgt cattattaaa     120
gacg                                                                  124

<210> SEQ ID NO 3
<211> LENGTH: 174
<212> TYPE: DNA
<213> ORGANISM: Bacillus anthracis Ba-murB2-D1

<400> SEQUENCE: 3
tgcattcata tataatgctc cgccaactga acctggaata ccacaagcga actcaagacc      60
cgttaagtta tggtctaacg caatacgtga tacgtcaata attgctgcac cgcactgtgc     120
tacaattgtc gttcctgtta cagtaacacc tgtaatatga attaaactta ctgt           174

<210> SEQ ID NO 4
<211> LENGTH: 145
<212> TYPE: DNA
<213> ORGANISM: Bacillus anthracis Ba-murB2-D2
```

```
<400> SEQUENCE: 4
aagttatggt ctaacgcaat acgtgatacg tcaataattg ctgcaccgca ctgtgctaca    60
attgtcgttc ctgttacagt aacacctgta atatgaatta aacttactgt aatcccgcga   120
attccaccgt ctttaataat gacat                                         145

<210> SEQ ID NO 5
<211> LENGTH: 96
<212> TYPE: DNA
<213> ORGANISM: Bacillus anthracis Ba-metRS1-H1

<400> SEQUENCE: 5
aatataactg gatctactac atttccttt gacttactca tctttccatc cttcattaaa    60
atccaaccgt gagcaaagac ttttttcgga agaggt                              96

<210> SEQ ID NO 6
<211> LENGTH: 107
<212> TYPE: DNA
<213> ORGANISM: Bacillus anthracis Ba-metRS1-H2

<400> SEQUENCE: 6
aacttatctg ccttttttac aggttcagca gatagtactt cagctacacg caattctact    60
ttaaagaaat catcaattgt aatttcttct gccttcggtc cttcttc                 107

<210> SEQ ID NO 7
<211> LENGTH: 103
<212> TYPE: DNA
<213> ORGANISM: Bacillus anthracis Ba-metRS1-H6

<400> SEQUENCE: 7
atccttcatt aaaatccaac cgtgagcaaa gactttttc ggaagaggta aatctaatgc    60
cattaaaatg attggccaat aaattgtatg gaaacgaacg att                     103

<210> SEQ ID NO 8
<211> LENGTH: 93
<212> TYPE: DNA
<213> ORGANISM: Bacillus anthracis Ba-metRS1-E4

<400> SEQUENCE: 8
ggttgtcctt tttctacttt tgttccagct ggaatacagc cgattgtaga taggcttccc    60
caagatgtat gtgcttcatc agtaaggcca agc                                 93

<210> SEQ ID NO 9
<211> LENGTH: 99
<212> TYPE: DNA
<213> ORGANISM: Bacillus anthracis Ba-uppS-UG9

<400> SEQUENCE: 9
tttaacgcga aattaagaat taatcccgta ttctctttcg tttcttccat ggccttctcc    60
atcgctctgc gtgtatgcgt aggaagacga tcttgttgc                           99

<210> SEQ ID NO 10
<211> LENGTH: 51
<212> TYPE: DNA
<213> ORGANISM: Bacillus anthracis Ba-uppS-UA3

<400> SEQUENCE: 10
cctctctttc tacacgcctc cgaatctgcg ccctctatgt tgaaagtctg t              51
```

```
<210> SEQ ID NO 11
<211> LENGTH: 103
<212> TYPE: DNA
<213> ORGANISM: Bacillus anthracis Ba-dfrA-2G1

<400> SEQUENCE: 11
ccaggcagtg gtctaccaat cgcttcatag ttttttcttc ccataataag cgggtgaccc      60
atcgttgttt tctttacata ctgcaattca ctcggtaaac gcc                      103

<210> SEQ ID NO 12
<211> LENGTH: 107
<212> TYPE: DNA
<213> ORGANISM: Bacillus anthracis Ba-dfrA-2G6

<400> SEQUENCE: 12
caggcagtgg tctaccaatc gcttcatagt ttttcttcc cataataagc gggtgaccca       60
tcgttgtttt ctttacatac tgcaattcac tcggtaaacg ccaaggt                  107

<210> SEQ ID NO 13
<211> LENGTH: 198
<212> TYPE: DNA
<213> ORGANISM: Staphylococcus aureus Sa-murB-E9

<400> SEQUENCE: 13
ccaccttcac ggataataat atttgagcca tttcctaaat atgtaacagg aatctcattt      60
tgataggcat atttaacaac tgcttgtact tcttcatttt tagtaggggt aatgtaaaag    120
tcggcattac cacctgtttt agtataagtg tatcgtttta aaggttcatc aactttaatt    180
ttttcatttg ggataagt                                                  198

<210> SEQ ID NO 14
<211> LENGTH: 169
<212> TYPE: DNA
<213> ORGANISM: Staphylococcus aureus Sa-murB-F7

<400> SEQUENCE: 14
cttgcaaatt agaatcttgt atcaatttac ctgcaaaatg accaggcggt ctttggaata      60
cactaccaca tgaaggatac tctaaaggtt gtttagattc tctacgttct gttaaatcat    120
ccattttagc ttgtatttca gtcatttac caggagctaa agtaaatgc                 169

<210> SEQ ID NO 15
<211> LENGTH: 146
<212> TYPE: DNA
<213> ORGANISM: Staphylococcus aureus Sa-murB-B9

<400> SEQUENCE: 15
accaattgaa cctggaatac cacatgcaaa ttcaaggcca gtaagtgcgt aatcacgagc      60
aacacgtgag acatcaataa ttgcagcgcc gctaccggct attatcgcat catcagatac    120
ttcgatatga tctagtgata ataaac                                         146
```

METHOD FOR IDENTIFYING DRUG-SENSITIZING ANTISENSE DNA FRAGMENTS AND USE THEREOF

RELATED APPLICATIONS

This application claims priority under §35 U.S.C. 119(e) from provisional application Ser. No. 60/782,961 filed Mar. 15, 2006, which is incorporated herein by reference in its entirety.

FIELD OF THE INVENTION

The present invention relates generally to bacterial diseases and more particularly to a methodology for the generation of bacterial strains useful in detecting the mechanism of action of antibacterial compounds and to determine genes and gene products that interact with existing antibiotics.

BACKGROUND INFORMATION

Antibiotics are useful agents in curing human and animal diseases caused by bacterial infections. Currently there are numerous antibiotics that control bacterial disease by interfering with a specific bacterial gene product, disrupting the biochemistry of the organism, and either preventing the organism from growing or killing the organism. However, antibiotic resistant strains of bacterial pathogens constantly emerge. Thus, there is a continual need to discover and develop new antibiotics effective against the new strains of pathogens. One way to find new agents is to discover and develop chemical compounds that act at a bacterial gene product not targeted by any current antibiotics. These potential targets for new antibiotics have been characterized as 'essential' by various methods that demonstrate the gene or gene product is required for bacterial growth. With the complete sequencing of the genomes of pathogens and various biochemical and microbiological analyses, numerous methodologies are available to define the set of 'essential' proteins in bacteria. Such proteins and the genes that encode them are prime targets for antibiotic development, as small molecule inhibitors of these functions can thereby serve to either stop the growth or to kill pathogenic bacteria in an infection.

Prior to genomic-based approaches, discovery and development of antimicrobial drugs relied upon the vast literature of bacterial physiology and biochemistry. For example, it has long been known that beta-lactam antibiotics inhibit and kill bacterial pathogens by interfering with the formation of the bacterial cell wall. The specific process inhibited by the beta-lactam antibiotics are the transpeptidation reactions that link peptidoglycan units in the final stages of cell wall biosynthesis. Transpeptidation is catalyzed by penicillin binding proteins (PBPs) encoded by bacterial genes. Thus, PBPs are validated targets for antibiotics and remain the subject of antibiotic discovery and development.

The peptidoglycan monomer unit is made by bacteria in a conserved biochemical pathway (FIG. 1). Each step of the process is catalyzed by a different bacterial protein that are encoded by corresponding genes including GlmU, MurA, MurB, MurC, MurD, MurE, MurF, MurG, MraY, and UppS. MurA is inhibited by the antibiotic fosfomycin, thus validating peptidoglycan biosynthesis as an essential process and qualifying the other individual proteins in the pathway as potential targets for new antibiotics. Genomic methods have confirmed the presence of these genes in all bacterial pathogens, further validating their potential as antibiotic targets.

Another set of known antibacterial targets are those enzymes used for bacterial protein synthesis. Many different useful antibiotics are known to act through inhibition of various steps of protein synthesis. One step requires the activity of tRNA synthetase enzymes that "charge" by means of covalent acylation a specific amino acid to its cognate tRNA molecule. These charged tRNAs are basic building blocks in protein synthesis. Inhibition of the charging process can severely limit protein synthesis. Small molecule inhibition of tRNA synthetases has been demonstrated, and certain inhibitors have been commercialized for use in antibacterial chemotherapy. For example, the commercial antibiotic mupirocin inhibits bacterial isoleucyl-tRNA synthetase. Many patents have been filed and granted on other chemical inhibitors of tRNA synthetase, including methionyl-tRNA synthetase.

Still another set of known antibacterial targets are those enzymes used for bacterial DNA synthesis. One biochemical required for DNA synthesis is tetrahydrofolate, a metabolite produced by the enzyme dihydrofolate reductase (DHFR). Thus, inhibition of DHFR can result in an antibiotic effect. The widely used antibiotic trimethoprim acts through selective inhibition of bacterial DHFR. Many patents concern the discovery and development of antibiotics having DHFR as the mechanism of action.

The present invention concerns the development of strains of bacteria that can be used to detect specific mechanisms of antibiotic action and thereby aid in antibiotic discovery and development. The method of creating the strains of bacteria involves generating and expressing antisense RNA that confers a hypersensitive phenotype to the bacteria that is specific for any particular antibiotic mechanism of action.

Experimental means have long been sought to modulate gene expression in bacteria. Conditional reduction in expression of target essential genes can make the host bacterium more sensitive to small molecules that inhibit the products of these genes. One way of doing this is to conditionally express RNA that is complementary to the mRNA transcribed from target genes. The formation of a double-stranded RNA species can result in blockage of translation or to degradation of the targeted mRNA. A substantial body of research has described the incidence of naturally occurring antisense post-transcriptional regulation in bacteria. Antisense regulation has been shown to be involved in the regulation of plasmid copy number, global regulation of cellular physiology, and to post-transcriptional regulation of certain cellular functions. These findings have inspired a number of efforts to experimentally create and exploit antisense regulation systems that can attenuate regulation of particular genes of interest. One experimental system was demonstrated as early as 1984 when researchers reported that portions of the lacZ gene, when expressed from an inducible promoter in the antisense direction, could cause specific and substantial attenuation of beta-glactosidase expressed from the lacZ gene. (Pestka, S. et al., (1984). Subsequently, others generated a histidine auxotroph phenotype by transforming *Mycobacterium smegmatis* with a plasmid containing an antisense fragment to its hisD gene ("Development and use of a conditional antisense mutagenesis system in mycobacterium." Parish T, and Stoker N G (1997), FEMS Microbiology Letters 154, 151-157). In another work ("Expression of an Antisense hla Fragment in *Staphylococcus aureus* Reduces Alpha-Toxin Production In Vitro and Attenuates Lethal Activity in a Murine Model." Kernodle et al., (1997) Infection and Immunity, 65, 179-184) a 600 base pair fragment of the hla gene was cloned in antisense orientation into a plasmid and transformed into *S. aureus*. The resulting strain made 16-fold less alpha-toxin thereby significantly blocking lethality of these cells in a murine infection model. A method described for the protist *Dictyostelium discoideum* used an un-regulated promoter to drive expression of random cDNAs in the antisense orientation in order to globally survey the resulting phenotypes of affected genes. ("Mutagenesis and gene identification in *Dictyostelium* by shotgun antisense" Spann et al. (1996) Proc. Natl. Acad. Sci. USA, 93, 5003-5007). By this method, numerous genes were functionally cataloged by the phenotypic effects of specific antisense-expressed cDNAs. These and other works demonstrate that certain antisense fragments cloned into suitable vectors can be used to alter bacterial strain phenotype by lowering the expression of specific genes in essential and non-essential metabolic pathways. The resulting inducer-dependent phenotype of the bacteria engineered with antisense genes includes results from altered metabolism, altered virulence, and reduced growth.

The "shotgun antisense" method described above for *Dictyoselium* could also be used to globally to survey for essential genes if an inducible promoter is used. In this way, resulting cells would not exhibit the resulting growth sensitivity until expression of the antisense DNA is turned on. Two similar but independently conducted antisense-based essential gene surveys were recently described ("Identification of critical Staphylococcal genes using conditional phenotypes generated by antisense RNA" Ji et al., (2001), Science 293: 2266-2269; "A genome-wide strategy for the identification of essential genes in *Staphylocccus aureus*" Forsyth et al., (2002) Molecular Microbiology 43:1387-1400). In both experiments, genomic DNA of *S. aureus* was purified, fragmented, and then "shotgun cloned" behind a plasmid-borne inducible promoter. After transformation of this shotgun library into *S. aureus*, resulting colonies were surveyed for growth in the presence or absence of inducer. Those that failed to grow due to expression of a gene fragment in the antisense orientation were collected and analyzed by DNA sequencing, and it was found that this pool of clones was highly enriched for known essential genes involved in such cellular functions as cell-wall biosynthesis, DNA replication, protein translation, RNA transcription, and fatty acid biosynthesis.

Other publications focused on antisense as a technique useful in identifying essential bacterial genes from an entire genome. Two patents were issued to Elitra Pharmaceuticals based on processes that were used in the Forsyth et al. publication above: U.S. Pat. No. 6,228,579 and U.S. Pat. No. 6,924,101, describe a process of surveying fragments of microbial genomic DNA for their capacity to reduce or block proliferation when expressed in the microorganism in the antisense orientation. The methods in the patent include fragmentation of genomic DNA from the organism of interest, cloning the fragments adjacent to an inducible promoter sequence on a plasmid, introducing the plasmid into the microorganism of interest, and comparing growth of the organism in the presence and absence of an inducer compound or stimulus that results in a dependent presence or absence of expression of the cloned fragment. Clones containing an antisense fragment that showed growth inhibition in the presence of inducer compound are selected, and the 'essential' gene for the clone is deduced by sequencing the antisense fragment. The presumption of these methods is that those fragments that cause reduction or blockage of proliferation of the microorganism do so by a mechanism that is specific to the function of the gene from which the fragment was derived, implying that this gene is one whose encoded cellular function is required for normal proliferation. Both patents state in their abstract and describe in their claims, "Antisense fragments that result in lethality when expressed indicate that the endogenous gene is a proliferation gene." Additional claims in the antisense patent literature include the method of using antisense-expression for screening compounds for the purpose of identifying specific inhibitors of the protein-target of the antisense, especially U.S. Pat. No. 6,924, 101.

While growth inhibition or lethality resulting in expression of an antisense fragment may be due to specific mRNA attenuation as described above, these phenotypes may also be due to unspecific mechanisms. Even though a gene fragment is expressed in the antisense orientation, it could still be translated to produce a toxic "cryptic peptide" that can inhibit growth (Lopes J M, Soliman N, Smith P K, Lawther R P, Mol Microbiol. 1989 August; 3(8): 1039-51. "Transcriptional polarity enhances the contribution of the internal promoter, ilvEp, in the expression of the ilvGMEDA operon in wild-type *Escherichia coli* K12"). Indeed, one analysis showed that substantial open reading frames can occur in the antisense orientation in many *E. coli* genes (Merino et al., (1994), "Antisense overlapping open reading frames in genes from bacteria to humans." Nucleic Acids Res. 22, 1903-1908). The prevalence of antisense-oriented coding regions could result in identification of ostensibly antisense-oriented gene fragments that cause unspecific growth sensitivity phenotypes. Another way in which RNA fragments can inhibit growth in ways other than by specific antisense-based mRNA attenuation is demonstrated by aptamers. (Ellington A D, Szostak J W, "In vitro selection of RNA molecules that bind specific ligands." Nature, 1990 Aug. 30; 346(6287):818-22; Blum, J H, Dove, S L, Hocschild, A, and Melalanos, J J (2000) "Isolation of peptide aptamers that inhibit intracellular processes" PNAS 97, 2241-2246). Such RNA fragments, which may be either in the sense or antisense orientation to the genes that they originated from, may actually form small molecules that may inhibit cellular functions entirely unrelated to the gene of origin In any instance of antisense growth inhibition, expression of antisense RNA fragments can result in bacterial strains that are hypersensitive to many different classes of chemical compounds unrelated to the target gene. Therefore, a limitation of current antisense methodology is that the resulting strains may not be attenuated for a specific metabolic pathway. A new method is needed in order to demonstrate a direct cause-and-effect mechanism for any particular growth-inhibiting antisense fragment.

Another limitation of current antisense methods involves the specificity of generating antisense to any given gene. This limitation is related to artifacts discussed above. Specifically, it is not possible at present to predict the required sequence and length of antisense RNA for any given gene that will produce the desired specific antisense effect. Hasan et al., ("Antisense RNA does not significantly affect expression of the galK gene of *Escherichia coli* or the N gene of coliphage lambda." Gene 72, 247-252) reported numerous failed attempts at producing a bona fide antisense effect despite three years of effort with many configurations of the genes and promoters. Hasan concludes that " . . . clear-cut regulation is more an exception than a rule (with antisense), and requires the use of a suitable gene and careful design, combined with strong conviction and good luck." This report demonstrates that simply cloning and expressing the inverted sequence of a gene will not reliably result in an antisense effect.

Another limitation of existing methodology concerns the use of genomic DNA as the source of the fragments for generating an antisense-based strains. First and foremost, existing methods define proliferation genes as those that generate a growth inhibited phenotype upon generation of an antisense strain to that gene. As indicated in the research cited, many antisense fragments will produce growth inhibition phenotype without connection to the gene from which it was derived. More importantly, targets for antibiotics that include these genes have in fact been defined by the integrated knowledge of bacterial genetics, physiology, and biochemistry. There have not been reports in the literature of an essential biochemical process identified using antisense that was not known through other means. Thus, it is inefficient to use genomic DNA fragmentation as the starting point for a method of constructing antisense-based sensitized strains for antibiotic discovery.

Second, the use of genomic DNA does not ensure that any particular gene will be adequately represented. The use of genomic DNA is biased towards genes with sequences that are more amenable to inhibition by antisense. Genes of equal value as antibiotic targets are each different in their susceptibility to antisense inactivation because of their different sequences and length. Because the gene fragment required for generating a specific antisense strain for a given gene cannot be specified, there is a significant risk that a useful antisense fragment will not be generated for any particular gene. To generate the number and diversity of fragments required to ensure a specific antisense strain will be represented for any particular gene, the use of genomic DNA is inappropriate. A bacterial genome may consist of several thousand genes, thus requiring millions of clones to be generated and examined.

Another limitation when using genomic DNA as a source for generating the fragments is that bacterial genomes often contain two or more copies of a gene encoding an essential function. Antisense to only one of these genes may not be sufficient to demonstrate a phenotype. For example, MurA in peptidoglycan biosynthesis is encoded by two different genes in many Gram-positive pathogens. The mode of action of the antibiotic fosfomycin is through inhibiting the MurA protein, demonstrating that MurA is an essential process. Antisense methodology as described in the literature on the whole genome would erroneously exclude MurA as an essential process.

One important process of antibiotic discovery is the determination of the mode of action for any given antibacterial compound. Mode of action determination can help differentiate those compounds with new and specific mechanisms of action from those compounds with non-specific or old modes of action. The utility of antisense in creating strains depleted in a particular target protein and thus sensitized to inhibitors of that target have been published. However, given that a particular target has been pre-selected for antibiotic discovery, it is inconvenient, inefficient, and incomplete to create any particular antisense-based strain using DNA from the entire genome. A new process is needed for specific work.

The identity of "proliferation" genes and other "essential" genes in bacteria has been accomplished a number of different ways and precede the use of antisense for this purpose.

Prior to genomics-based methods, microbial processes such as cell wall biosynthesis, protein synthesis, isoprenoid biosynthesis, and tetrahydrofolate synthesis were known to be useful sites of antibiotic action. Tools to track mode of action for antibiotics targeting these processes are useful in antibiotic discovery and development.

The presence of a gene fragment in antisense orientation can cause inducer-dependent growth-inhibited phenotype by mechanisms other than post-transcriptional reduction in mRNA. The potential for artifacts makes the selection of growth-inhibited phenotype an insufficient criterion for selecting specific antisense strains.

Many limitations exist for the methods of creating antisense-based hypersensitive strains for antibiotic discovery, including gene-specific requirements for antisense structure (sequence and length), an inconvenient cloning requirement to ensure adequate representation for any given gene, and multiple genes encoding essential processes.

Current published methods for generating antisense-based strains for detecting mode of action are subject to artifact, and are inconvenient, inefficient, and incomplete for use in antibiotic drug discovery.

SUMMARY OF THE INVENTION

The invention provides a method for generating and selecting drug-sensitizing antisense DNA fragments. In one embodiment, the method includes identifying a gene of interest using knowledge of bacterial physiology, biochemistry, genetics, genomics, and other means. The method includes PCR amplification of a gene of interest using genomic DNA as a template; fragmentation of the DNA by sonication or other means; selecting DNA fragments no longer than 400 base pairs; ligating the DNA fragments into a suitable expression plasmid with a selectable marker; transforming the plasmids containing the DNA fragments into the organism from which the gene of interest originated; and selecting clones from transformed cells that show a phenotypic difference of the clone grown in the presence of the inducer relative to the phenotype in the absence of inducer.

In another embodiment, the invention provides that the discernible phenotype is growth rate; relative sensitivity to a growth inhibiting compound; requirement for addition of a nutrient to the growth medium; morphology such as shape; relative sensitivity to osmotic stress, or colony size, for example.

In another embodiment, the invention provides a method for selecting bacterial strains containing specific drug-sensitizing DNA fragments including selecting those strains wherein the inserted DNA fragment is oriented antisense to some portion of the gene of interest selecting those strains wherein the mRNA level of the organism in the presence of inducer is less than 25% of the levels in the absence of inducer; selecting those strains according to the method of the invention wherein the magnitude of the phenotype is dependent on the concentration of the inducer.

BRIEF DESCRIPTION OF FIGURES

FIG. 2 shows a process for identification of specific antisense fragments.

FIG. 3 shows a validation process for specific sensitized antisense strains

FIG. 4B shows an EC50 shift for Rx19 in six different MetRS antisense clones. Clones HI, 112, H6, and E4 showed EC50 shifts for Rx19 greater than 4. Clones A3 and A5 showed EC50 shifts less than 4 even though all six clones had xylose-dependent growth inhibited phenotype and inserts with fragments antisense to the MetRS gene.

FIG. 9 is a table of antisense fragments.

DETAILED DESCRIPTION OF THE INVENTION

Definitions

Figure 1:
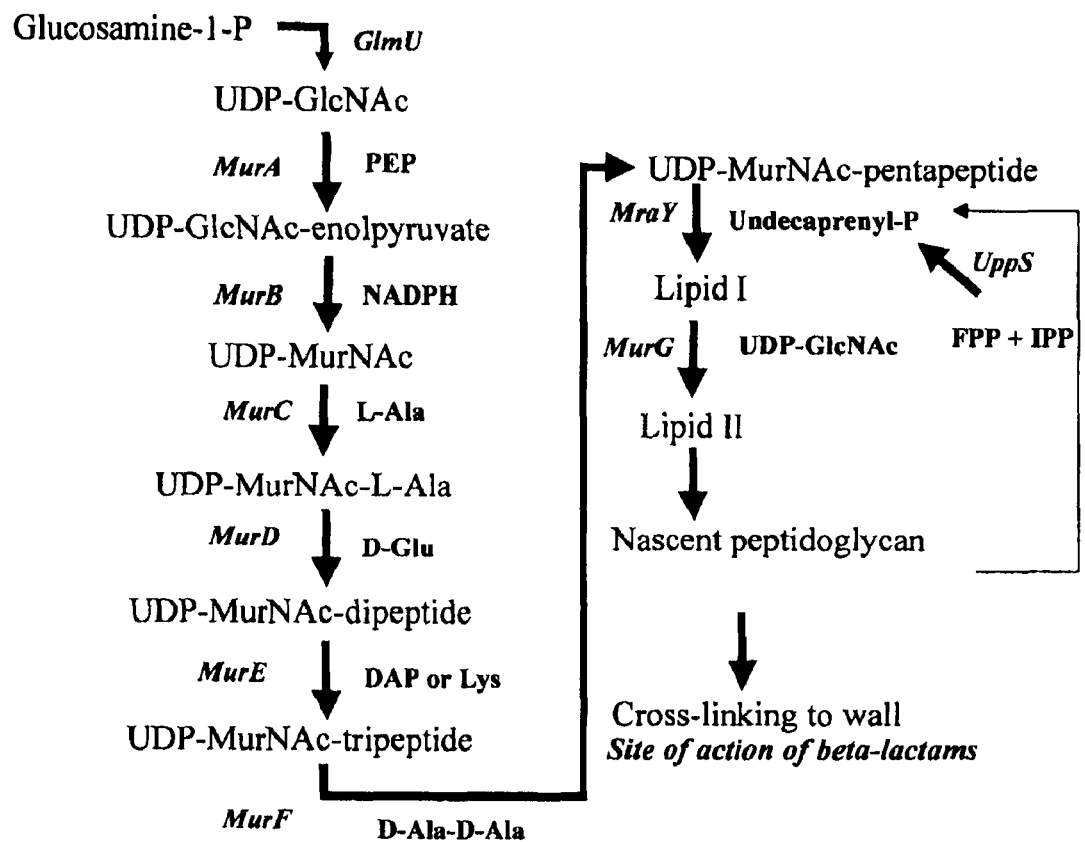
FIG. 1 shows a peptidoglycan biosynthetic pathway in bacteria.

"Beta-lactam" A beta-lactam (p-lactam) is a lactam with a heteroatomic ring structure, consisting of three carbon atoms and one nitrogen atom. The beta-lactam ring is part of several antibiotics, such as penicillin, which are therefore also called beta-lactam antibiotics. These antibiotics work by inhibiting the bacterial cell wall synthesis. Examples of beta-lactam antibiotic classes include penicillins, cephalosporins, and cabapenems.

"Antibiotic" is a compound used to control infections. Examples of antibiotics include Cell wall inhibitors include: Beta-lactams include (penicillin G, penicillin V, nafcillin, methicillin, oxacillin, cloxacillin, dicloxacillin, flucloxacillin, ampicillin, amoxacillin, carbenicillin, ticarcillin, azocillin, mezlocillin, pipericillin, Cephalosporins, cephalothin, cefazolin, cefalexin, cefuroxime, cefamandole, cefoxitin, cefaclor, moxalactam, cefaperazone, ceftazidime, ceftriaxone, clavulanic acid, sulbactam, imipenem, aztreonam, Cefoxitin, cefozolin, Cefaclor).

Inhibitors of peptidoglycan biosynthesis, Inhibitors of GlmU, MurA (Fosfomycin) Inhibitors of MurB (dihydropyrrolones), Inhibitors of Undecaprenyl pyrophosphate Synthetase (hydantoins, sulfonamides), Inhibitors of LpxC (UDP-3-O-acyl N-acetylglycosamine deacetylase), Lipopeptides (daptomycin), Isoprenoid biosynthesis inhibitors (bacitracin, phosmidomycin), Fatty acid biosynthesis inhibitors (cerulenin, triclosan, isoniazid) Protein synthesis inhibitors, aminoglycosides (streptomycin, gentamicin and kanamycin), tetracyclines, chloramphenicol, macrolides (erythromycin, azithromycin, clarithromycin), lincosamides (lincomycin and clindamycin), and oxazolidinones (linezolid) tRNA synthetase inhibitors such as mupirocin, MetRS inhibitors (catechols, prolines, quinolones), Peptide deformylase inhibitors (hydroxamates), RNA synthesis inhibitors such as rifampicin, DNA gyrase inhibitors such as quinolones (nalidixic acid, ciprofloxacin) Antifolates (trimethoprim and sulfamethoxazole), "EC50" and "IC50" mean the concentration of compound resulting in 50% of the growth rate of the organism compared to the untreated control.

A general protocol for generating and selecting antisense-encoding DNA fragments is shown in FIG. 2. A general protocol for validating those clones with specific antisense response is shown in FIG. 3.

Our interest in antisense has been in development of specific antisense strains of Bacillus anthracis and of Staphylococcus aureus for use in tracking the mechanism of action of new antibiotic candidates. To overcome limitations in the current methods antisense methods, we developed the method outlined in FIGS. 2 and 3. Unlike previous methods that used a limited number of antisense fragments for any given gene to generate antisense strains, we select a single gene based on its validated utility as an antibiotic target site. We then generate a population of fragments of limited length for cloning into an expression vector. This process results in a large number of transformants, only a small subset of which has the inducer-dependent growth-inhibited phenotype. This subset requires additional selection using (1) inducer-dependent decrease in the level of mRNA for the target and (2) inducer-dependent hypersensitivity to a growth-inhibiting compound as a second criterion. Finally, the selective inducer concentration (SIC) is determined that gives the maximal sensitivity to the antibiotic. The resulting strains that are selected after passing all of the criteria are selectively hypersensitive to compounds specifically inhibiting the target gene or gene product of the antisense or to compounds inhibiting processes directly linked to the target gene or gene product.

It is not obvious that such a method should be required for producing such useful mode of action tools, because previous publications indicate that many antisense fragments should work and that the only criterion necessary for selection is an inducer-dependent growth inhibition. Thus, the frequency of artifact in antisense is not appreciated. This method is novel because it begins with the target gene identified in advance and requires the generation of thousands of fragments from which to begin selection of those that will generate the desired drug sensitized strain.

The identities of the isolated genes were verified by sequencing and then subjected to sonication. The fragment sizes were monitored by agarose gel electrophoresis to verify the fragments were less than 200 bp in length. The DNA fragments were endpolished, ligated into the SmaI site of pBAX-2, and rescued by transformation in E. coli DH5. Resulting libraries were amplified in dam–/dcm– E. coli INV110 (Invitrogen). Amplified library DNA was electroporated into B. anthracis plasmid-less strain UM123C1-1. Randomly selected transformants were tested for insert size by PCR. The range of insert sizes was 100-400 bp. About 2000 resulting colonies (CFU) per library were screened for growth sensitivity in BHI medium with or without added xylose inducer at 2% final concentration. Plasmid DNA from these colonies was analyzed by DNA sequencing to determine the sequence and orientation relative to the xylose inducible promoter and to the gene of interest.

TABLE 1

| Gene | Enzyme | Total CFU | Number of colonies growth inhibited in 2% xylose medium | Inserts of growth-sensitive clones with "antisense" orientation | Inserts of growth-sensitive clones with "Sense" orientation |
| --- | --- | --- | --- | --- | --- |
| murB-2 | MurB | 2024 | 26 | 26 | 0 |
| metRS1 | MetRS | 2208 | 40 | 39 | 1 |
| uppS | UppS | 2150 | 26 | 23 | 3 |
| dfrA | DHFR | 2304 | 21 | 15 | 6 |

EXAMPLES

We have built specifically-sensitized antisense strains using validated antibiotic targets. Four example targets are MurB (UDP-N-acetylenolpyruvoylglucosamine reductase [EC: 1.1.1.15 8]) in peptidoglycan biosynthesis (FIG. 1), methionyl-tRNA synthetase [EC: 6.1.1.10] in protein synthesis, UppS in peptidoglycan biosynthesis (undecaprenyl diphosphate synthase [EC:2.5.1.31]), and DHFR (dihydrofolate reductase [EC:1.5.1.3]) in DNA biosynthesis. The DNA sequences of these genes in B. anthracis, S. aureus, and many other microbial genomes are widely available (for example, in the Kyoto Encyclopedia of Genes and Genomes (KEGG), http://www.genome.jp/kegg/genes.html.

Each of these four genes was subjected to the process outlined in FIGS. 2 & 3. Table 1 shows the outcome of the process for each gene, including the number of transformants selected, the number of transformants demonstrating growth inhibition phenotype in the presence of the inducer (xylose) relative to the growth in the absence of inducer, the number of clones with inducer-dependent growth-inhibited phenotype, and the number of growth-inhibited phenotype clones with plasmid inserts in the "antisense" and the "sense" orientation relative to the promoter. Most of the strains with a growth-inhibited phenotype in the presence of inducer had inserts in the antisense orientation, but there were a significant number of strains that had inserts in the sense orientation. This result demonstrates that the method for selecting gene fragments for an essential gene requires process steps not previously known to be required.

Table 1. B. anthracis strain performance featuring fragments from B. anthracis genes subjected to process in FIG. 2 and FIG. 3. PCR amplification of DNA for each gene was performed using oligonucleotides sequences based on the published sequences for the corresponding B. anthracis gene.

Figure 4A:
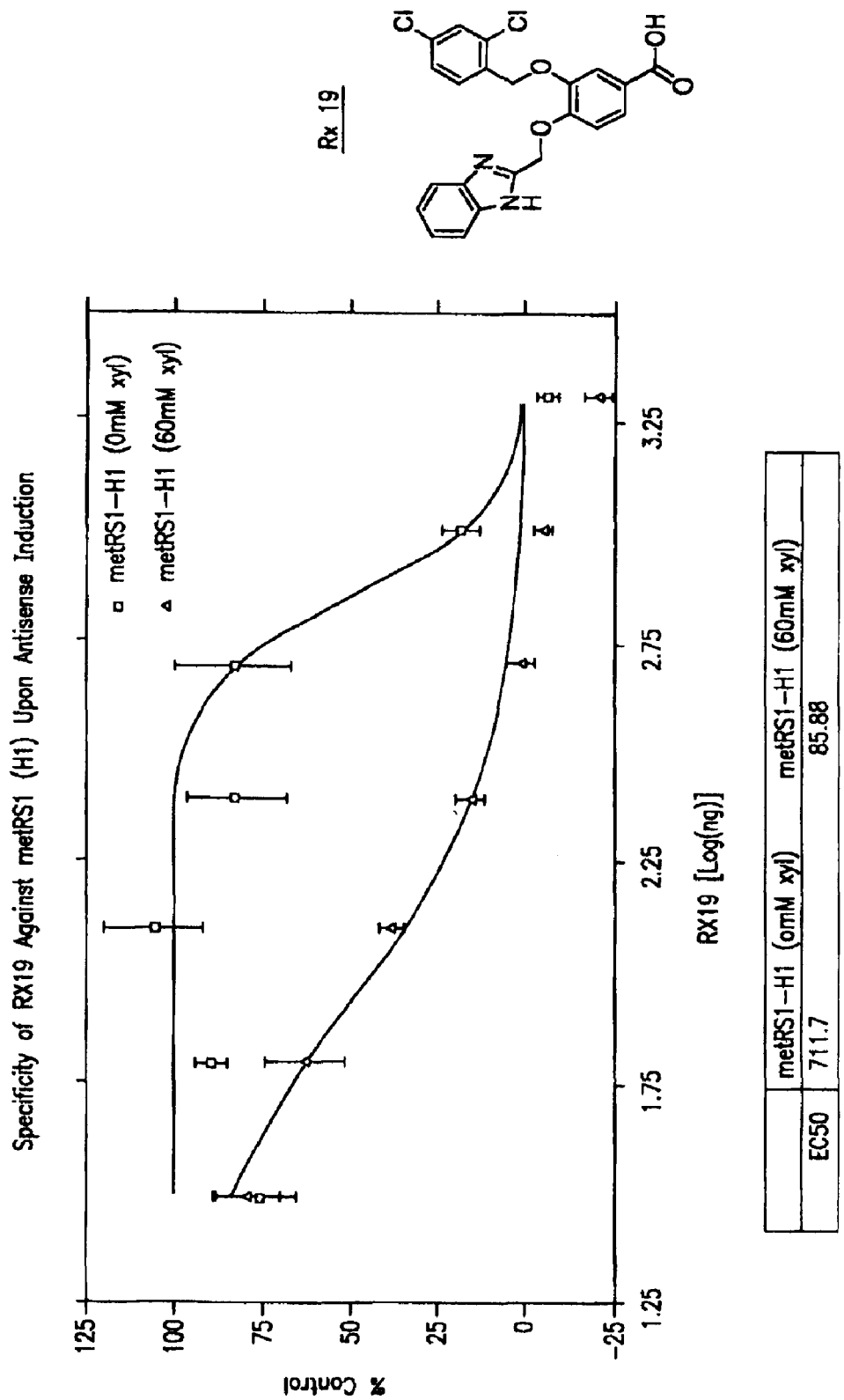
FIG. 4A shows a EC50 Shift Sensitivity of MetRSl antisense clones to the specific MetRS inhibitor Rx19. (a) Characterization of growth inhibition curve in the presence and absence of xylose. One of the antisense clones (HI) was characterized as to its sensitivity to the MetRS-specific inhibitor Rx19. Upper line: no xylose added. Lower line: +60 mM xylose. The EC50 concentration for each condition was determined. The "EC50 shift" is defined as the ratio of the EC50 in the absence and in the presence of xylose. The EC50 shift in this experiment is calculated to be 711/85.8=8.3. (b) EC50 shift for Rx19 in six different MetRS antisense clones. Clones HI, H2, H6, and E4 showed EC50 shifts for Rx19 greater than 4. Clones A3 and A5 showed EC50 shifts less than 4 even though all six clones had xylose-dependent growth inhibited phenotype and inserts with fragments antisense to the MetRS gene.

Table 1 includes results for methionyl-tRNA synthetase (MetRS) encoded by the metRS1 gene. Subjecting this gene to the protocols in FIG. 2 resulted in approximately 2,000 strains containing DNA fragments of the metRS1 gene. Of these, 40 showed growth inhibited phenotype upon exposure to the inducer xylose. Of these, 39 contained inserts antisense to the metRS1 gene. The antisense strains were then characterized in terms of the inducer-dependence of their growth attenuation and their sensitivity to a specific inhibitor of MetRS (Rx19) (FIG. 3), and their sensitivity to a panel of antibiotics (FIG. 4A). Many of the strains were selectively hypersensitive to Rx19. RT-PCR experiments verified that in the presence of inducer, the mRNA for metRS1 was reduced in level compared to the mRNA level for metRS1 in the absence of inducer. Levels of other mRNAs were not reduced. Some of the strains showed no difference in sensitivity to antibiotics. These strains are likely growth-attenuated due to a mechanism other than specific post-transcriptional mRNA reduction. These strains are not useful for detecting antibacterial compounds.

Figure 5:
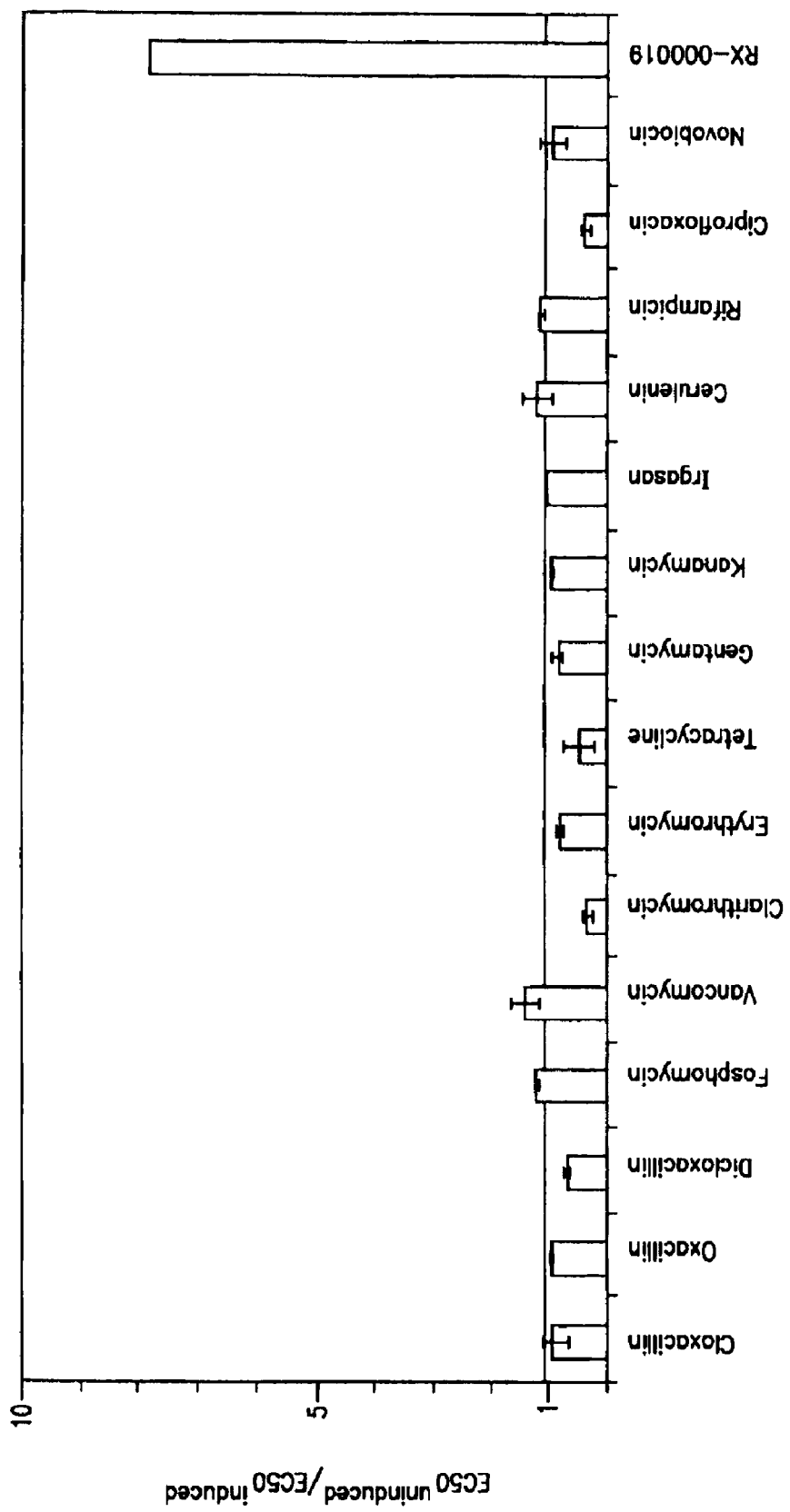
FIG. 5 shows an EC50 shifts for MetRS antisense clone HI on a panel of antibiotics. The sensitivity of MetRS antisense clone to various antibiotics was determined in the absence and presence of xylose. With one exception, the clone showed the same sensitivity to antibiotics in the absence or presence of xylose. For Rx19, the clone was about 8 fold more sensitive in the presence of xylose relative to the sensitivity in the absence of xylose.
Figures 6A, 6B:
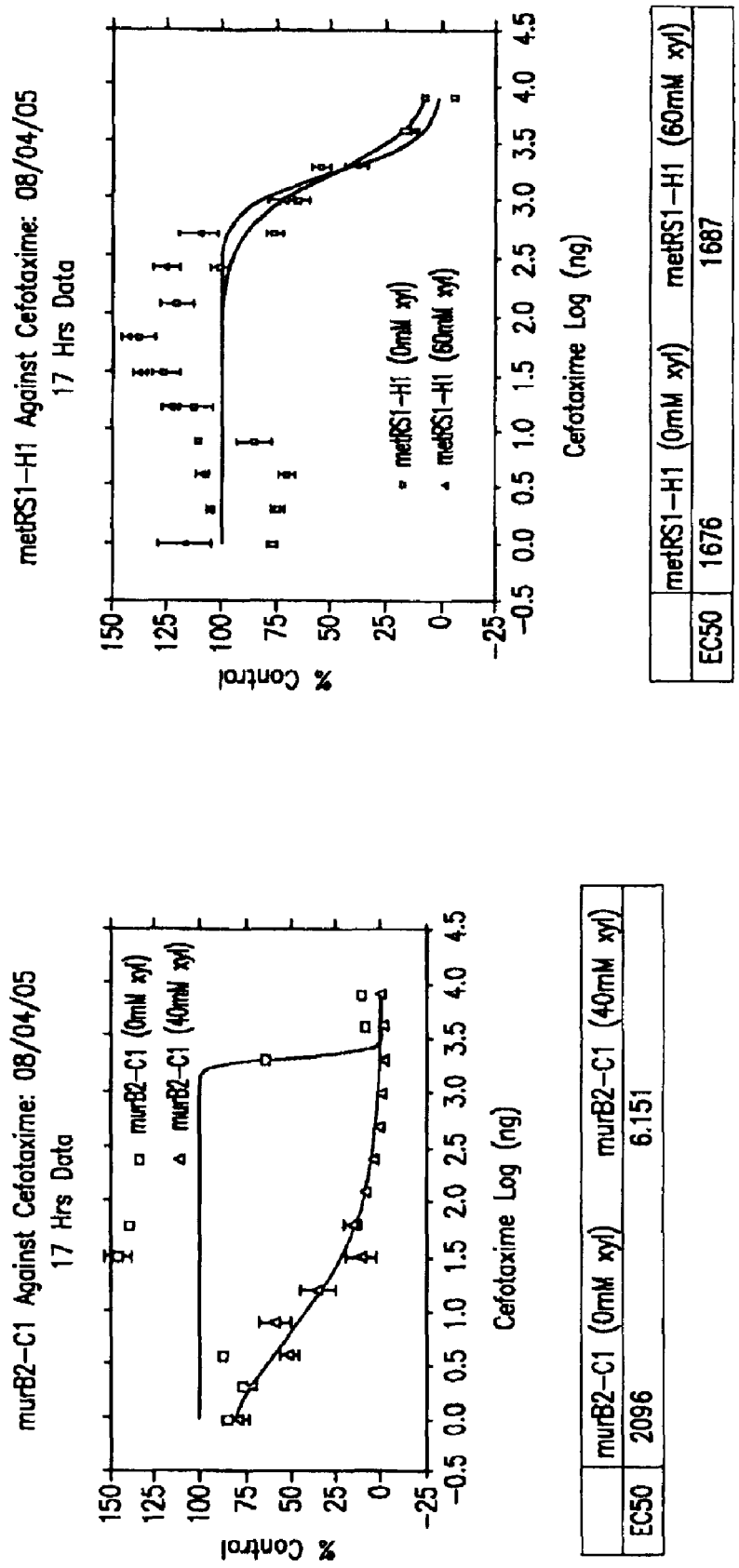
FIGS. 6A and 6B show the response of murB2 antisense clone to cefotaxime in the presence and absence of a subinhibitory concentration antisense inducer. Upper line: no inducer. Lower line: +40 mM xylose, (a): murB2 antisense clone, (b) metRS antisense clone. The ratio of the IC50+xylose/EC50 (−xylose) gives the 'IC50 shift'. In (a) the shift is computed to be (2096/6.1)=343. In (b), the metRS antisense clone showed no difference in sensitivity to cefotaxime, indicating that the cefotaxime mechanism of action is unrelated to metRS.
Figure 7A:
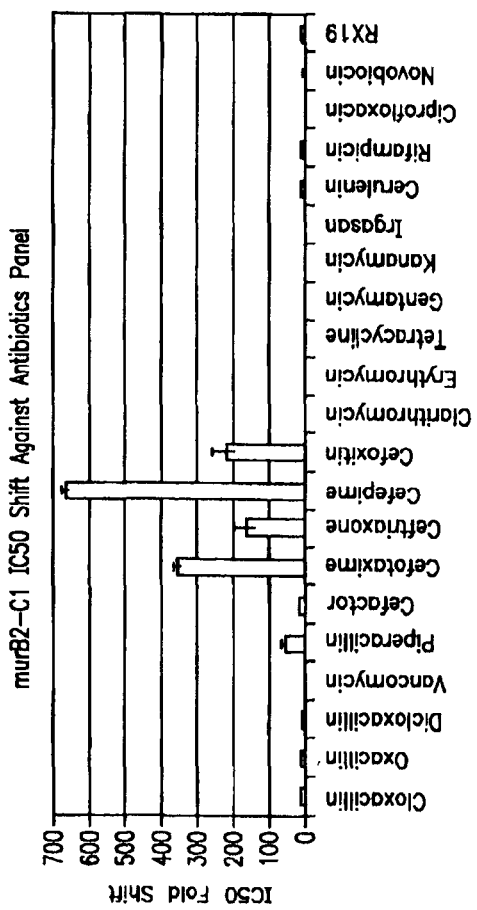
FIGS. 7A and 7B show B. anthracis murB-2 antisense strain sensitivity to cephalosporins and other antibiotics, (a) antibiotic panel including cefotaxime, ceftriaxone, cefepime, and cefoxitin, all of which showed greater than 100 fold shift in IC50 in the presence of xylose, (b) antibiotic panel showing greater than 4-fold shift in IC50 for cloxacillin, oxacillin, dicloxacillin, and cefaclor.
Figure 7B:
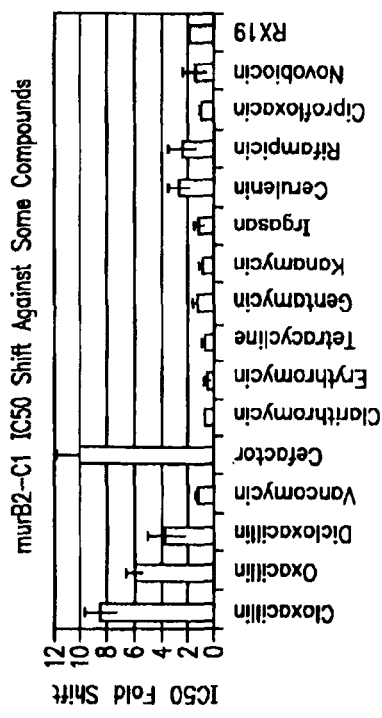

Table 1 also shows results for the MurB target, the second step of peptidoglycan biosynthesis (FIG. 1). All bacterial pathogens require MurB; however, there are currently no antibiotics that act by inhibiting MurB. Subjecting the functional B. anthracis murB gene (murB-2) to the protocols in FIG. 2 resulted in approximately 2,000 strains containing DNA fragments of the murB gene. Of these, 26 showed growth inhibited phenotype upon exposure to the inducer xylose. Of these, 26 contained inserts antisense to the murB-2 gene. The strains were then characterized in terms of the inducer-dependence of their growth attenuation and their sensitivity to a panel of antibiotics. Many of the strains were selectively hypersensitive to cell wall inhibiting antibiotics (FIG. 5 and FIG. 6A). RT-PCR experiments verified that in the presence of inducer, the mRNA for murB-2 was reduced in level compared to the mRNA level for murB-2 in the absence of inducer. Levels of other mRNAs were not reduced.

Some of the strains showed no difference in sensitivity to antibiotics. These strains are likely growth-attenuated due to a mechanism other than specific post-transcriptional mRNA reduction. These strains are not useful for detecting mechanism of action of antibacterial compounds.

Example 1

Figure 10:
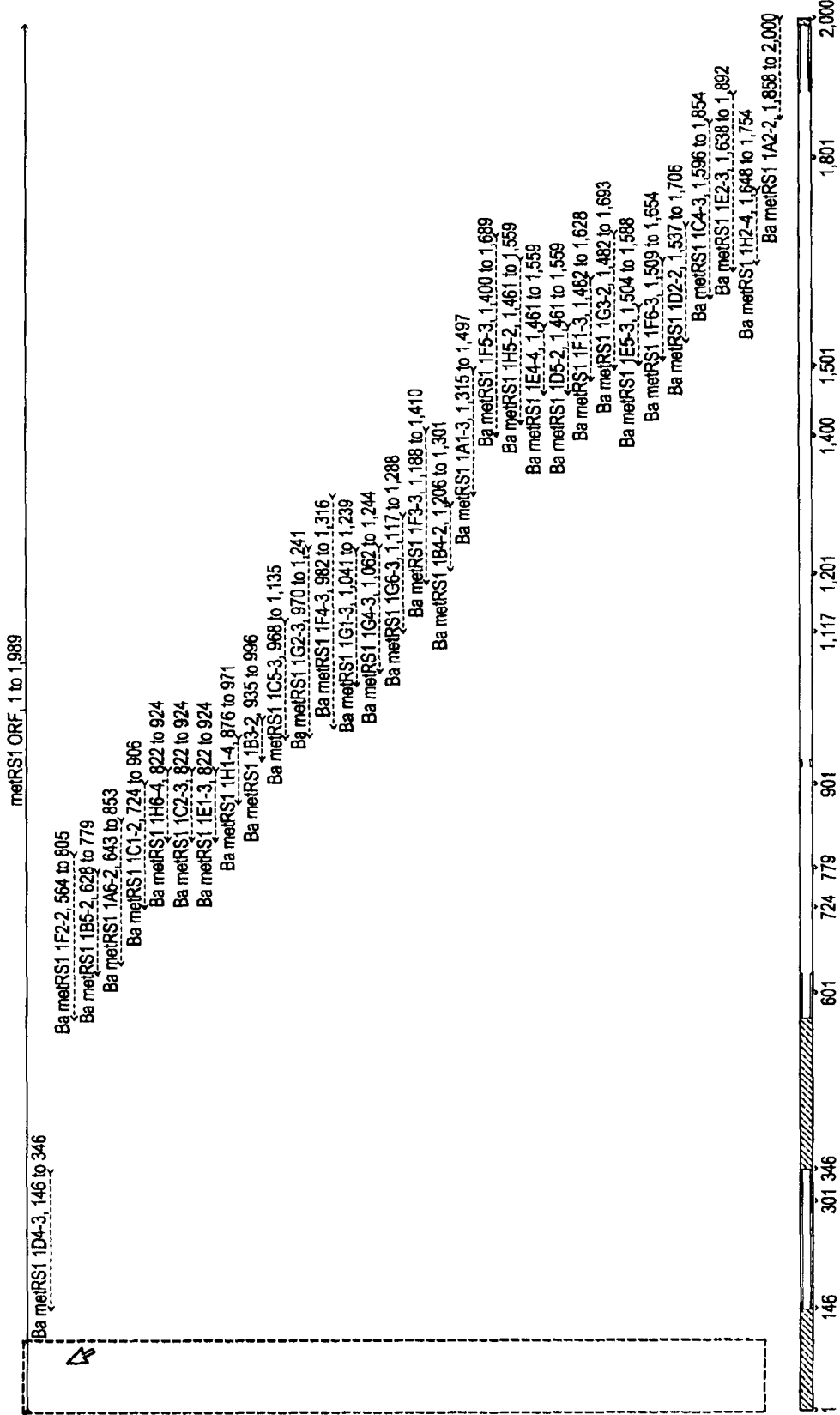
FIG. 10 shows a graphic map of xylose-responsive growth inhibitory fragments corresponding to the B. anthracis metRS-1 (metS) gene open reading frame (ORF).

FIG. 10 shows a graphic map of xylose-responsive growth inhibitory fragments corresponding to the *B. anthracis* metRS-1 (metS) gene open reading frame (ORF). All fragments were found to be in the antisense orientation (leftward pointing arrow) relative to the corresponding gene (rightward pointing arrow). Numbers after the name of each antisense DNA fragment correspond to the span and position of the fragment relative to the gene sequence.

Example 2

Figure 11:
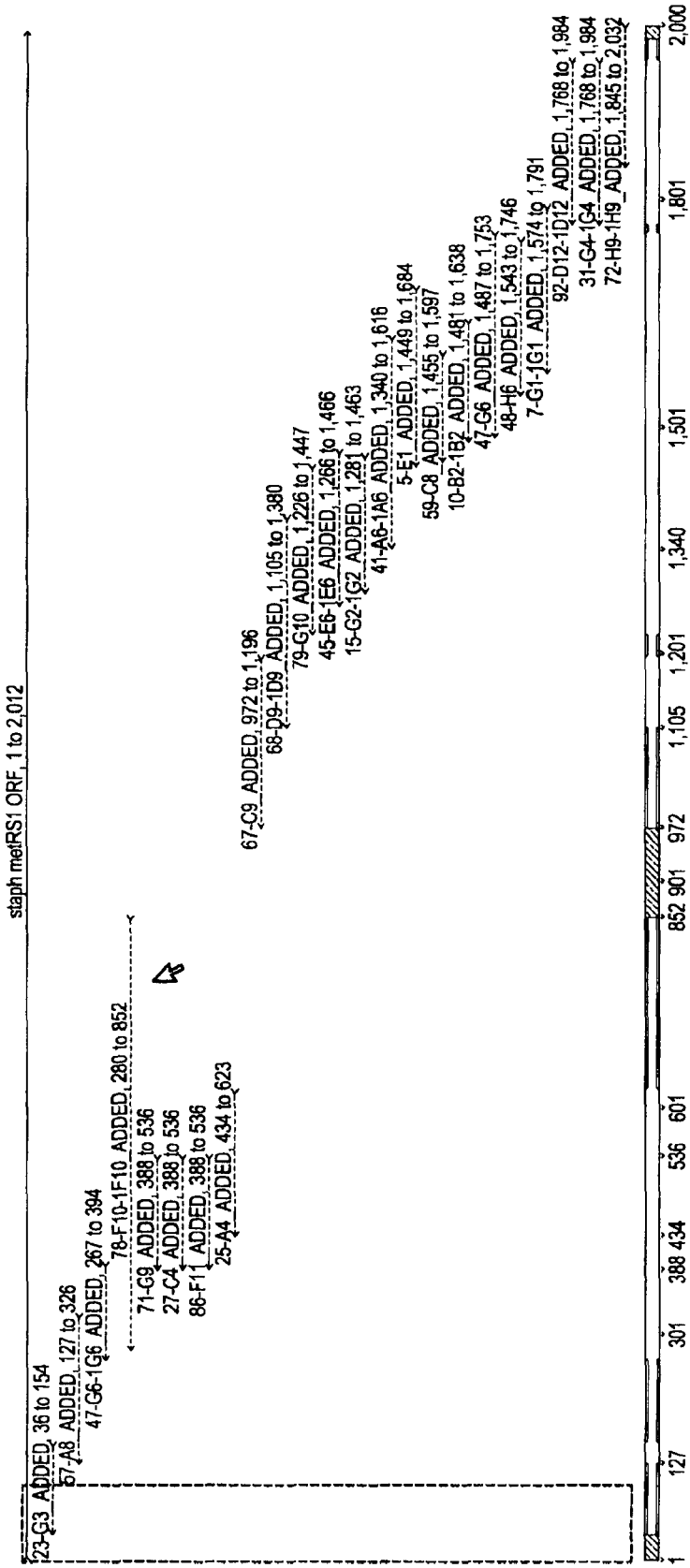
FIG. 11 shows a graphic map of xylose-responsive growth inhibitory antisense fragments corresponding to the S. aureus metRS (metS) gene open reading frame (ORF).

FIG. 11 shows a graphic map of xylose-responsive growth inhibitory antisense fragments corresponding to the *S. aureus* metRS (metS) gene open reading frame (ORF). All fragments were found to be in the antisense orientation (leftward pointing arrow) relative to the corresponding gene (rightward pointing arrow). Numbers after the name of each antisense DNA fragment correspond to the span and position of the fragment relative to the gene sequence.

Example 3

Figure 12:
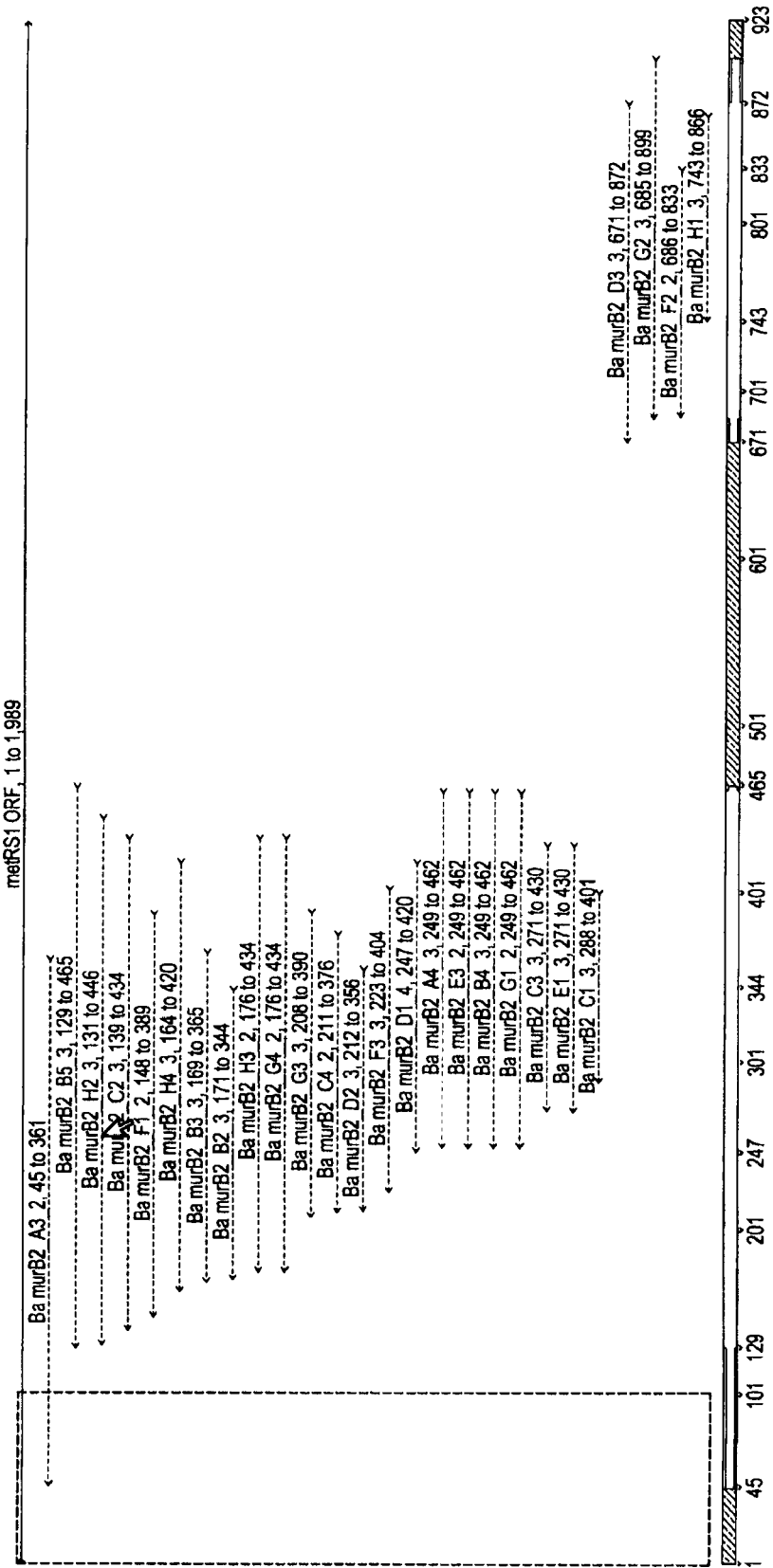
FIG. 12 shows a graphic map of xylose-responsive growth inhibitory antisense fragments corresponding to the B. anthracis murB-2 gene open reading frame (ORF).

FIG. 12 shows a graphic map of xylose-responsive growth inhibitory antisense fragments corresponding to the *B. anthracis* murB-2 gene open reading frame (ORF). All fragments were found to be in the antisense orientation (leftward pointing arrow) relative to the corresponding gene (rightward pointing arrow). Numbers after the name of each antisense DNA fragment correspond to the span and position of the fragment relative to the gene sequence.

Example 4

Figure 13:
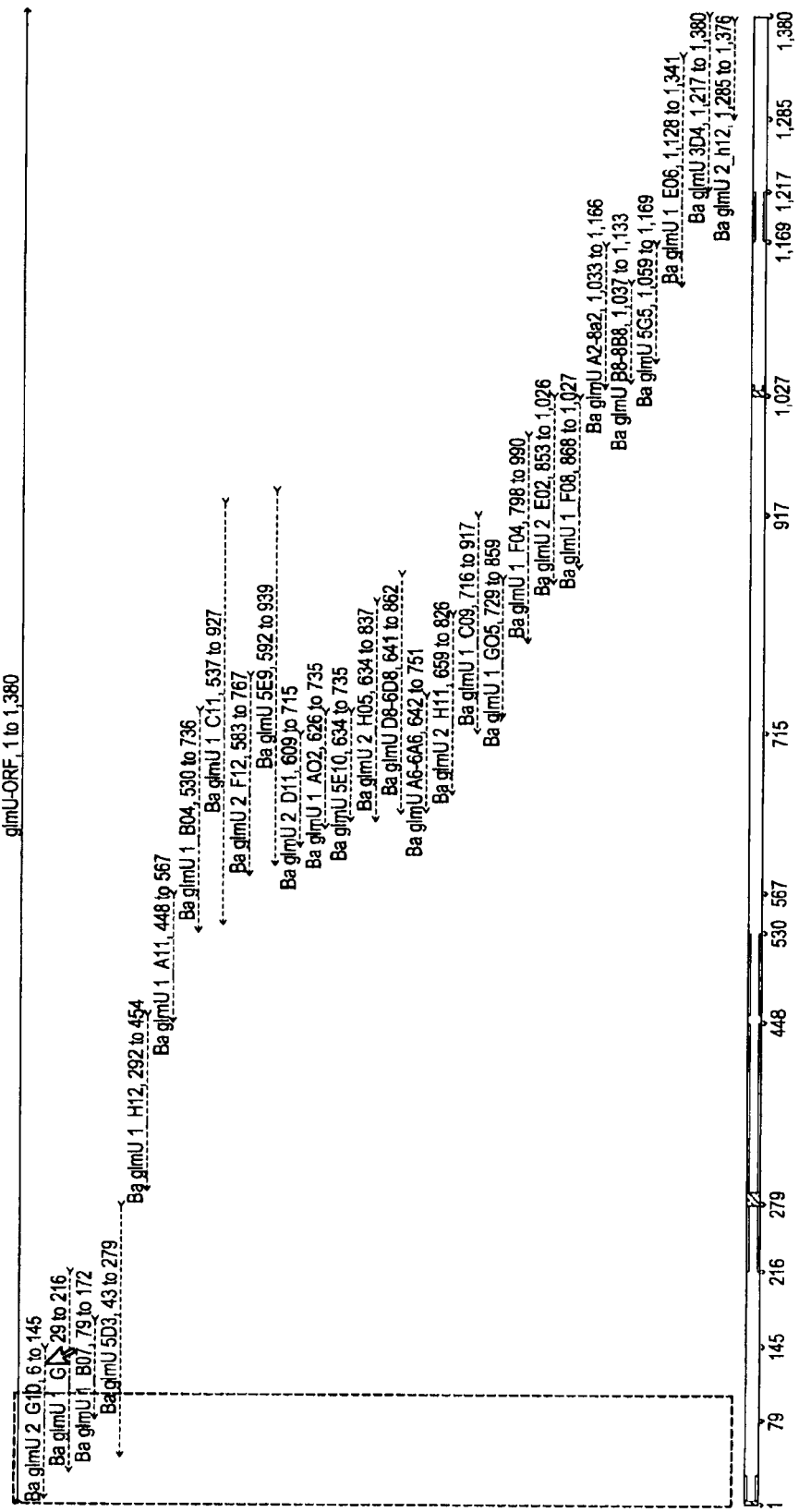
FIG. 13 shows a graphic map of xylose-responsive growth inhibitory fragments corresponding to the B. anthracis glmU gene open reading frame (ORF).

FIG. 13 shows a graphic map of xylose-responsive growth inhibitory fragments corresponding to the *B. anthracis* glmU gene open reading frame (ORF). All fragments were found to be in the antisense orientation (leftward pointing arrow) relative to the corresponding gene (rightward pointing arrow). Numbers after the name of each antisense DNA fragment correspond to the span and position of the fragment relative to the gene sequence.

Example 5

Figure 14:
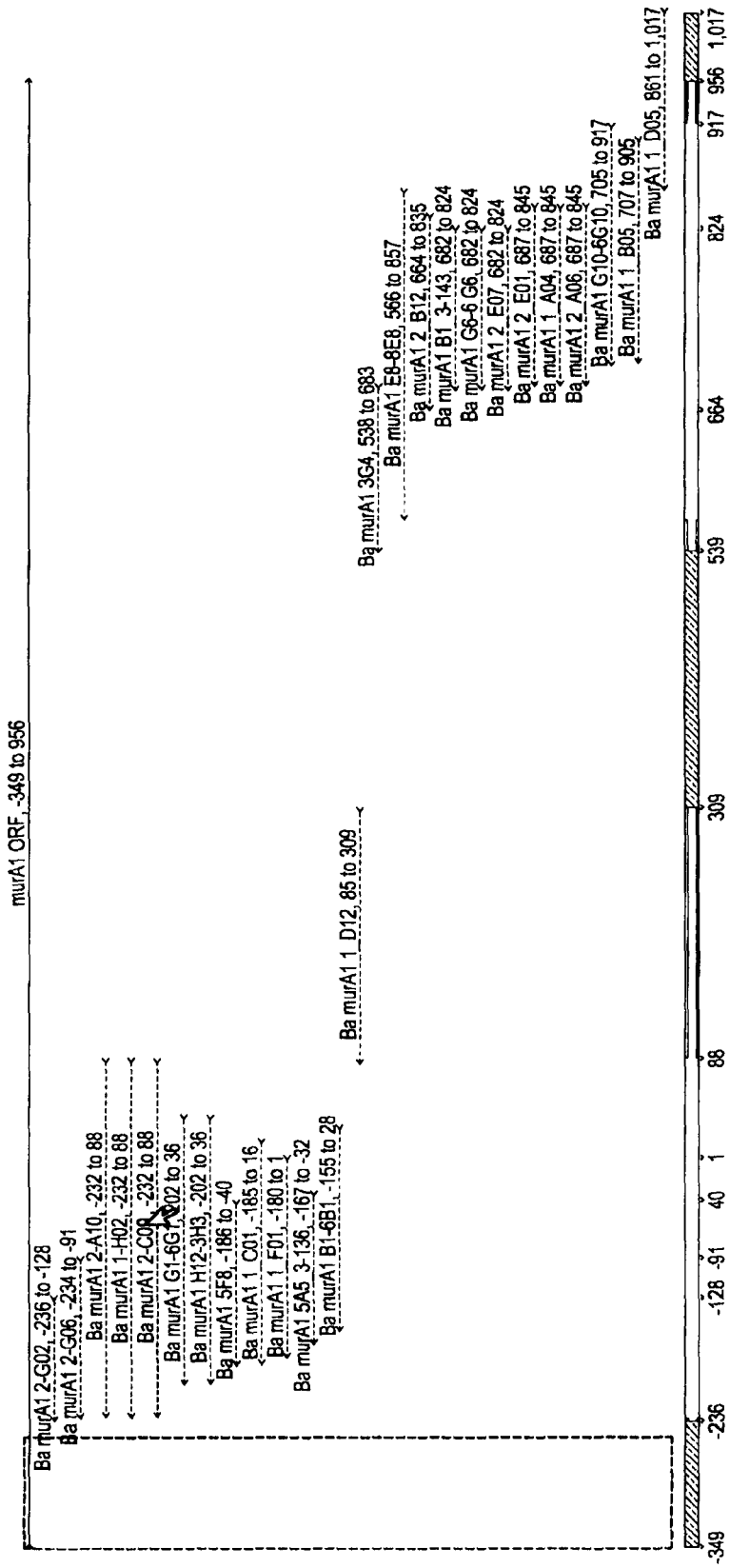
FIG. 14 shows a graphic map of xylose-responsive growth inhibitory antisense fragments corresponding to the B. anthracis murAl gene open reading frame (ORF).

FIG. 14 shows a graphic map of xylose-responsive growth inhibitory antisense fragments corresponding to the *B. anthracis* murAl gene open reading frame (ORF). All fragments were found to be in the antisense orientation (leftward pointing arrow) relative to the corresponding gene (rightward pointing arrow). Numbers after the name of each antisense DNA fragment correspond to the span and position of the fragment relative to the gene sequence.

Example 6

Figure 15:
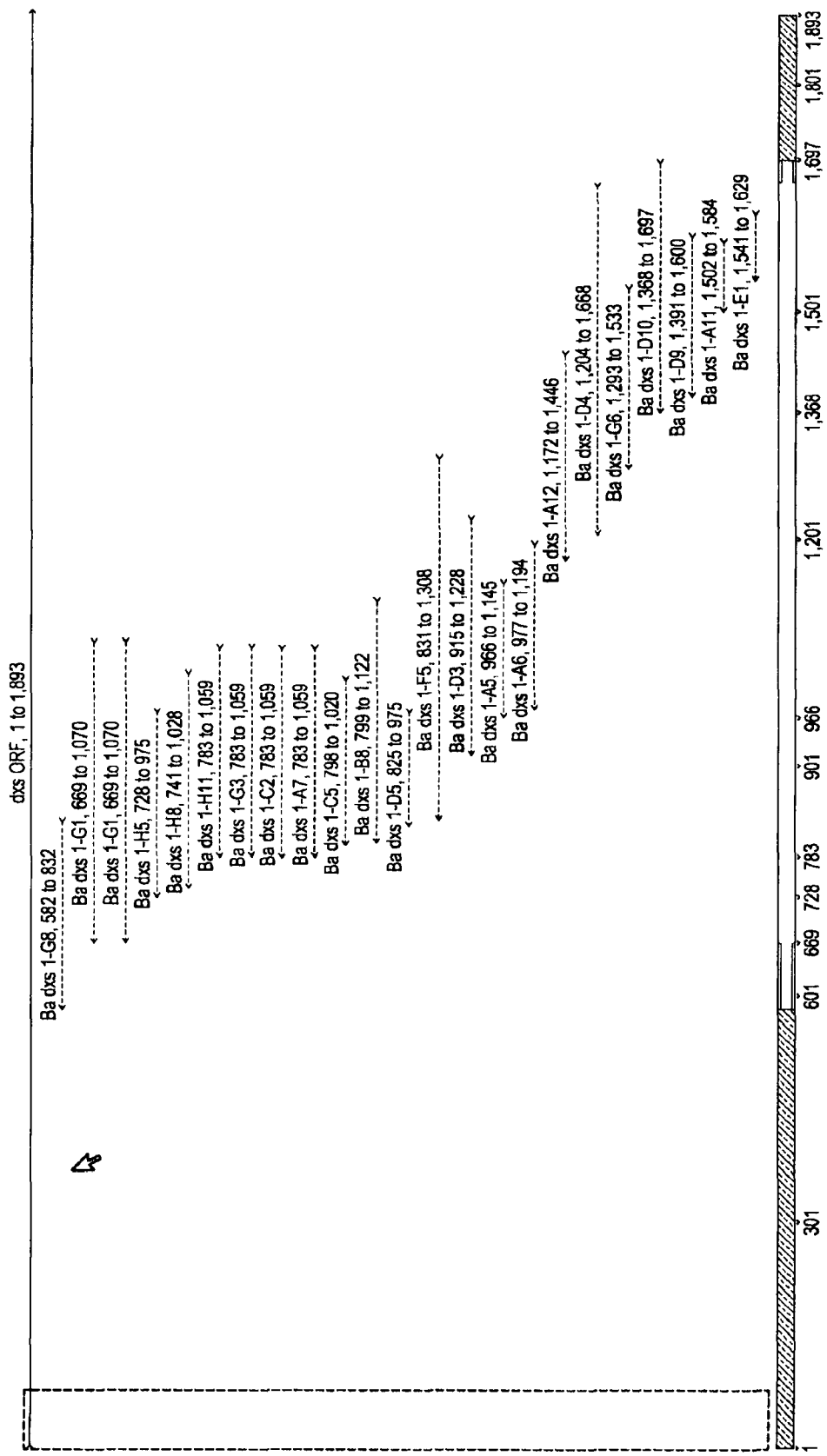
FIG. 15 shows a graphic map of xylose-responsive growth inhibitory fragments corresponding to the B. anthracis dxs gene open reading frame (ORF).

FIG. 15 shows a graphic map of xylose-responsive growth inhibitory fragments corresponding to the *B. anthracis* dxs gene open reading frame (ORF). All fragments were found to be in the antisense orientation (leftward pointing arrow) relative to the corresponding gene (rightward pointing arrow). Numbers after the name of each antisense DNA fragment correspond to the span and position of the fragment relative to the gene sequence.

Example 7

Figure 16:
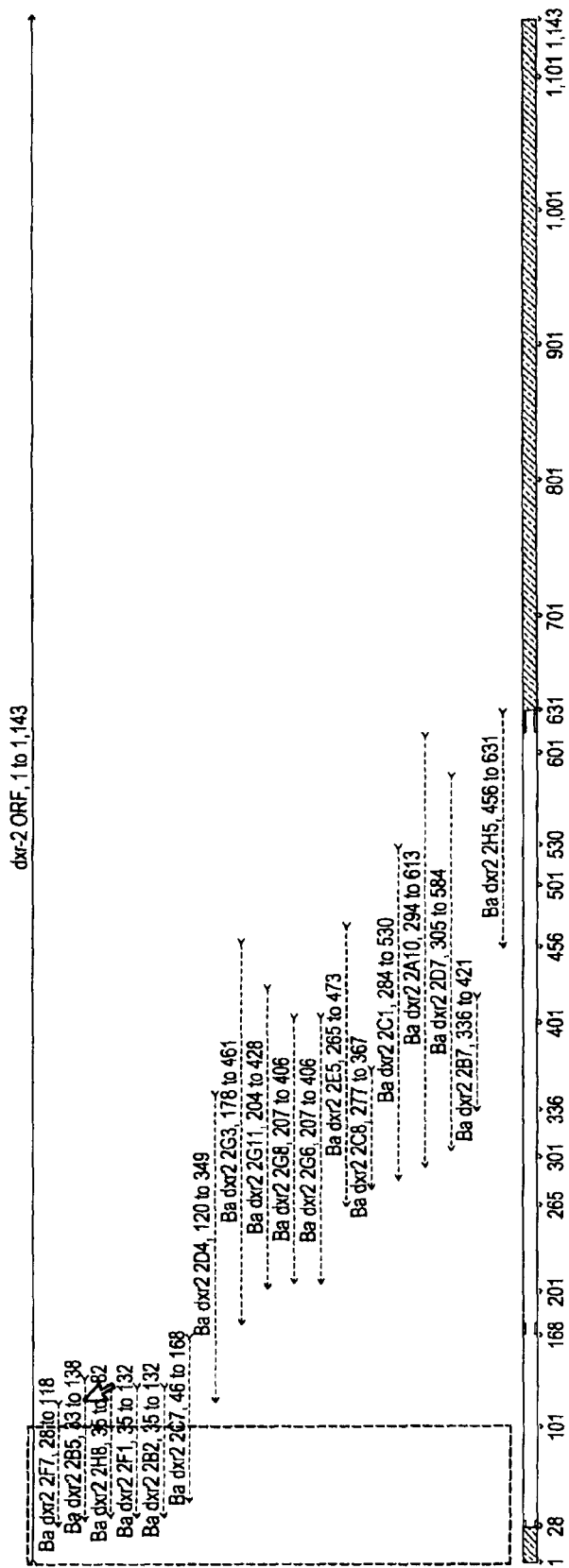
FIG. 16 shows a graphic map of xylose-responsive growth inhibitory fragments corresponding to the B. anthracis dxr-2 gene open reading frame (ORF).

FIG. 16 shows a graphic map of xylose-responsive growth inhibitory fragments corresponding to the *B. anthracis* dxr-2 gene open reading frame (ORF). All fragments were found to be in the antisense orientation (leftward pointing arrow) relative to the corresponding gene (rightward pointing arrow). Numbers after the name of each antisense DNA fragment correspond to the span and position of the fragment relative to the gene sequence.

Example 8

Figure 17:
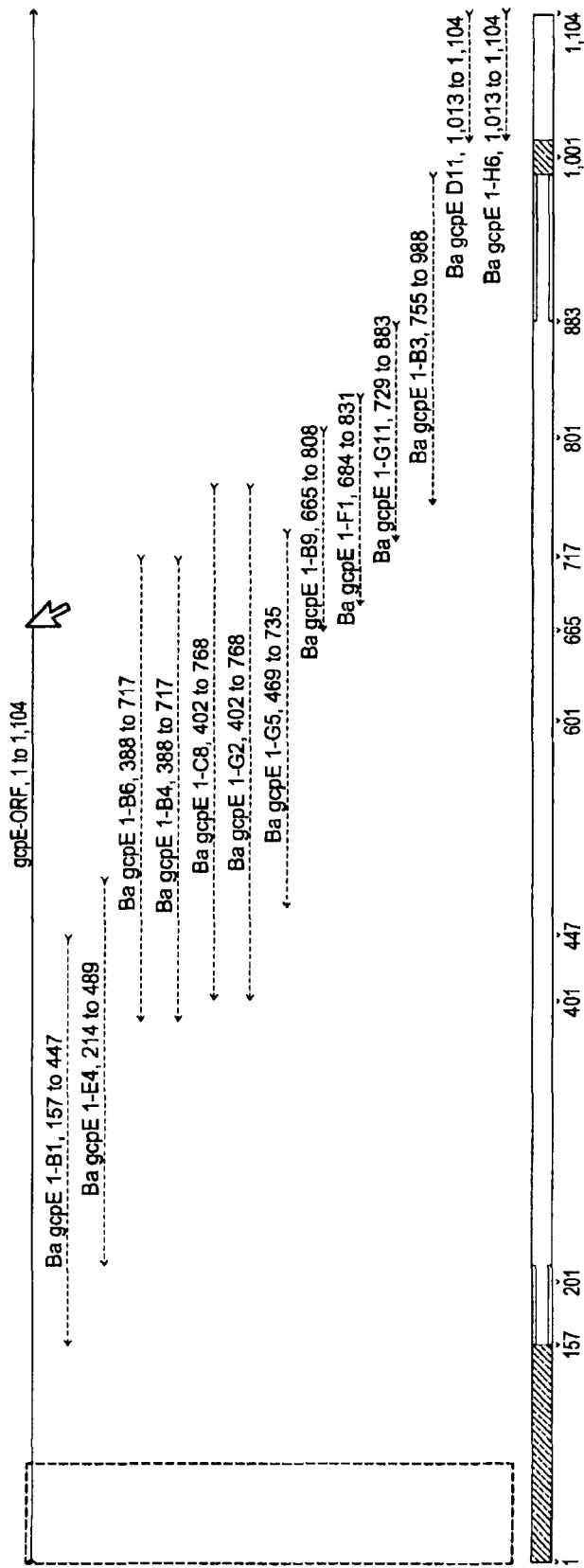
FIG. 17 shows a graphic map of xylose-responsive growth inhibitory fragments corresponding to the B. anthracis gcpE gene open reading frame (ORF).

FIG. 17 shows a graphic map of xylose-responsive growth inhibitory fragments corresponding to the *B. anthracis* gcpE gene open reading frame (ORF). All fragments were found to be in the antisense orientation (leftward pointing arrow) relative to the corresponding gene (rightward pointing arrow). Numbers after the name of each antisense DNA fragment correspond to the span and position of the fragment relative to the gene sequence.

Example 9

Figure 18:
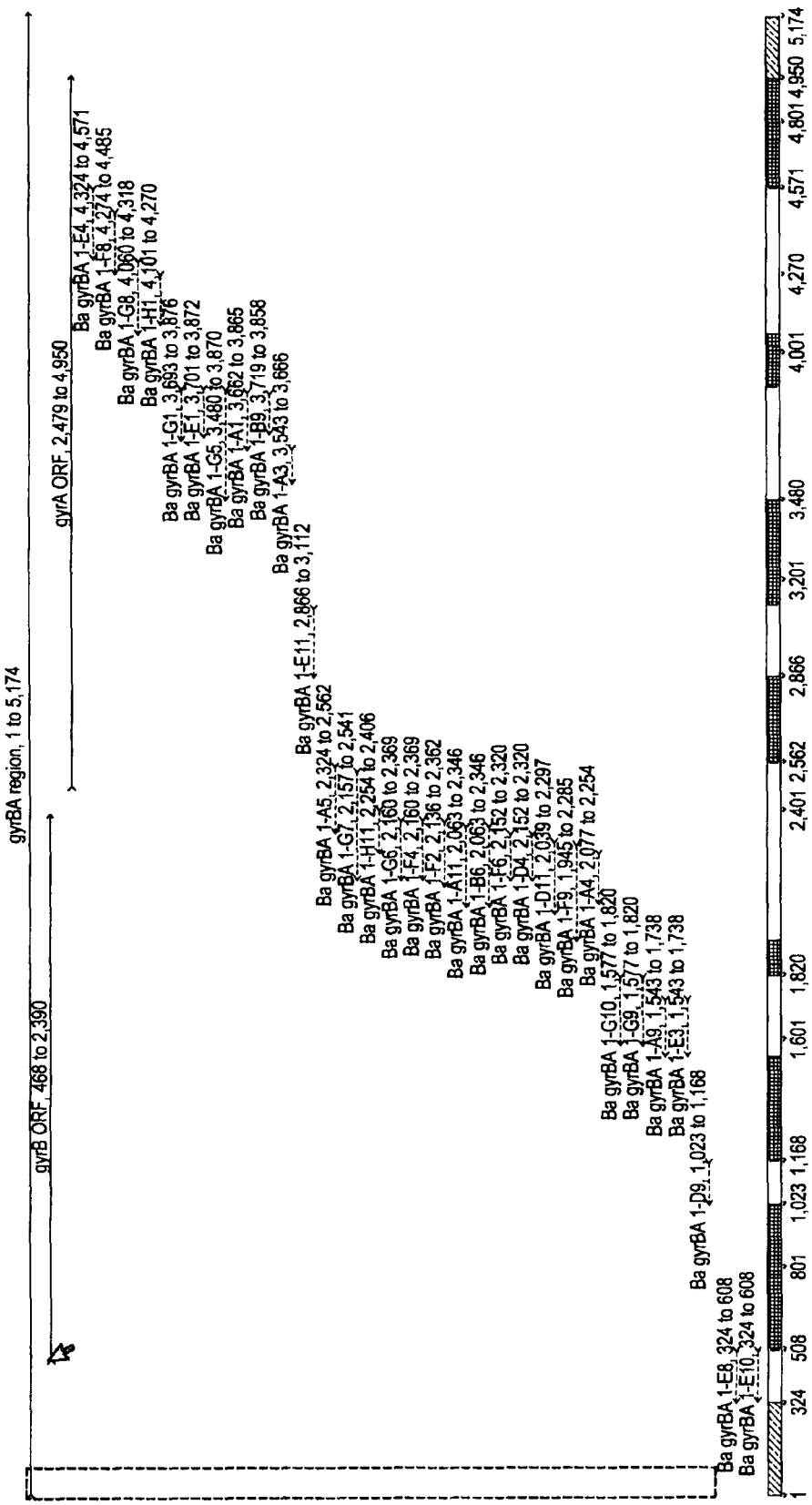
FIG. 18 shows a graphic map of xylose-responsive growth inhibitory fragments corresponding to the 5. anthracis gyrB andgyrA gene open reading frames (ORF).

FIG. 18 shows a graphic map of xylose-responsive growth inhibitory fragments corresponding to the 5. *anthracis* gyrB andgyrA gene open reading frames (ORF). All fragments were found to be in the antisense orientation (leftward pointing arrow) relative to the corresponding gene (rightward pointing arrow). Numbers after the name of each antisense DNA fragment correspond to the span and position of the fragment relative to the gene sequence.

Example 10

Figure 19:
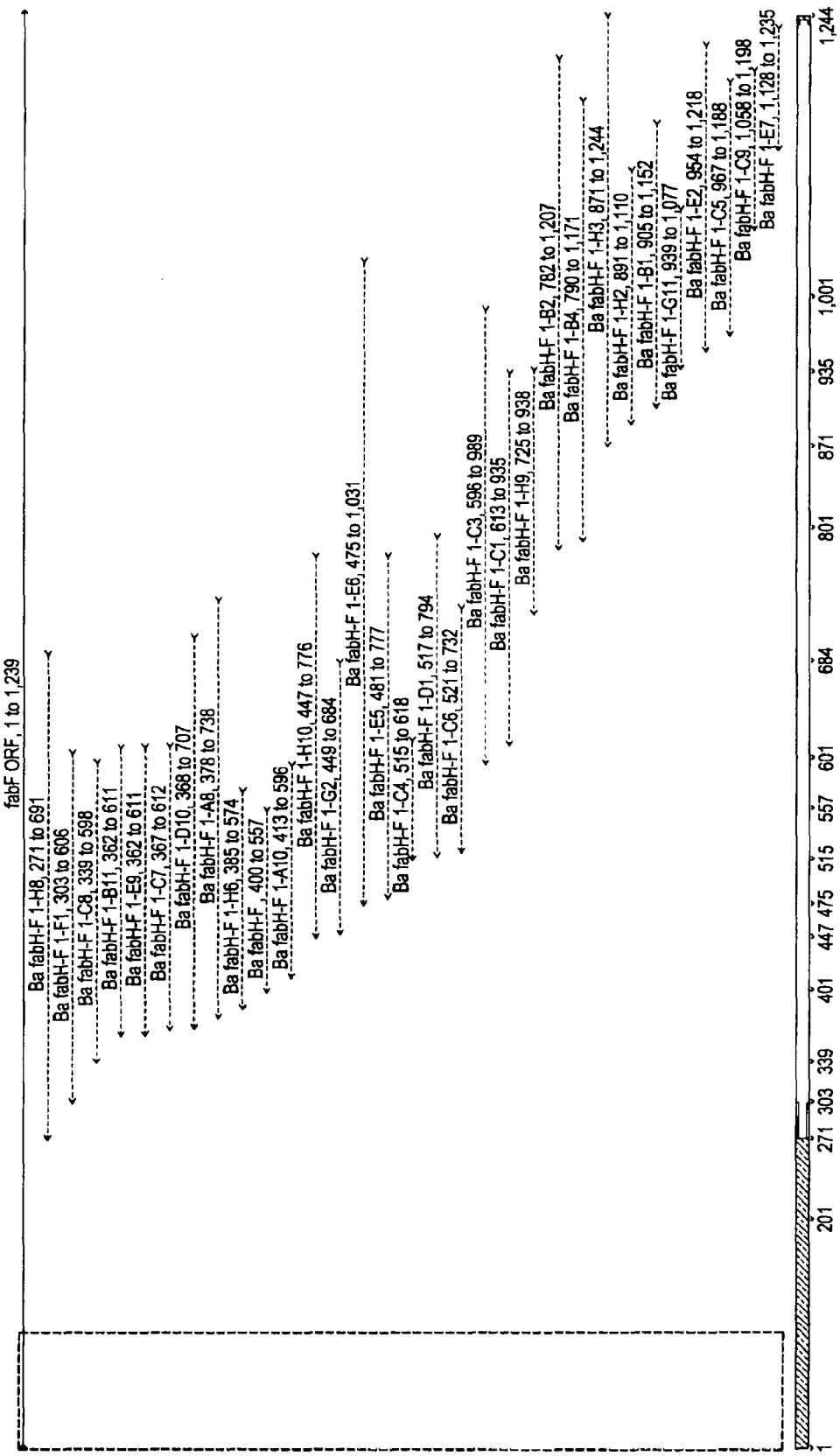
FIG. 19 shows a graphic map of xylose-responsive growth inhibitory fragments corresponding to the B. anthracis fabF gene open reading frame (ORF).

FIG. 19 shows a graphic map of xylose-responsive growth inhibitory fragments corresponding to the *B. anthracis* fabF gene open reading frame (ORF). All fragments were found to be in the antisense orientation (leftward pointing red arrow) relative to the corresponding gene (rightward pointing green arrow). Numbers after the name of each antisense DNA fragment correspond to the span and position of the fragment relative to the gene sequence.

Figures 8A, 8B:
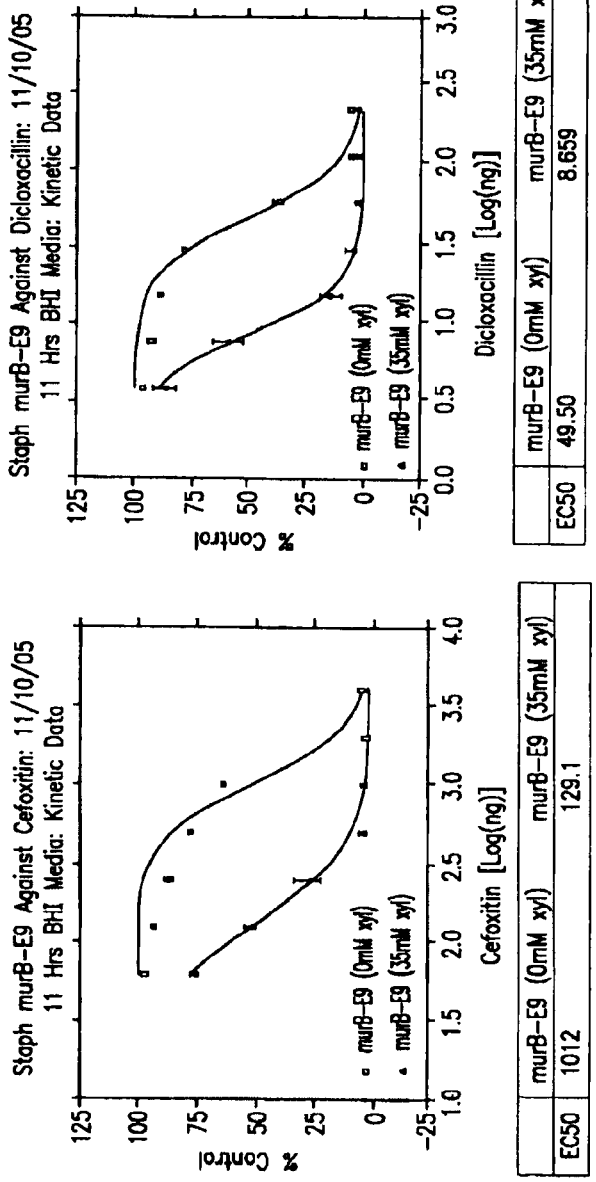
FIGS. 8A-8C show an antibiotic dose response in the presence and absence of xylose for S. aureus engineered with murB antisense. (a) Cefoxitin IC50 shift is computed to be 1012/129.1=7.8. (b) Dicloxacillin IC50 shift is computed to be 49.5/8.6=5.8. (c) Antibiotic panel IC50 shift for S. aureus murB antisense strain showing 4-fold or greater sensitivity to cloxacillin, oxacillin, dicloxacillin, pipericillin, cefotaxime, ceftriaxone, cefepime, cefoxitin, and cefozolin.
Figure 8C:
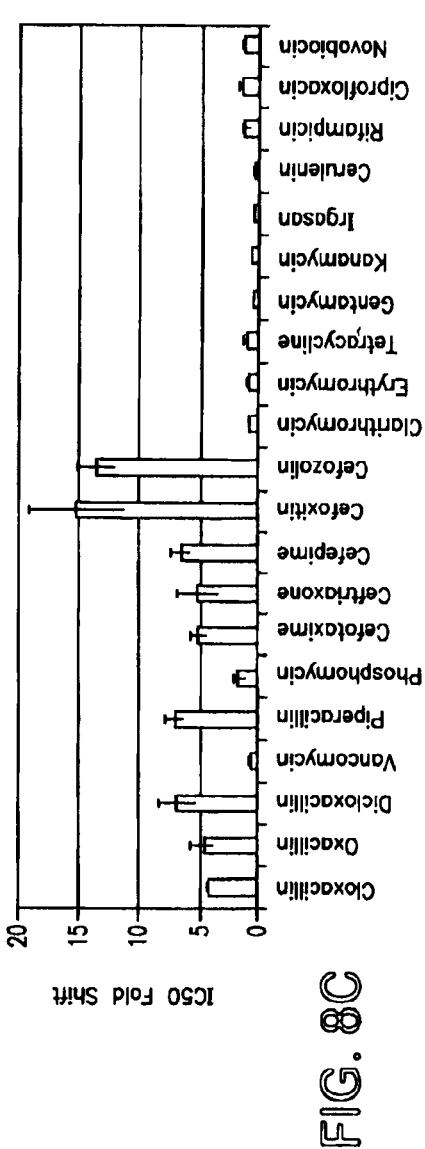

The method described in FIGS. 2 & 3 can produce antisense strains in *S. aureus* similar to those in *B. anthracis*. FIGS. 8 A-C shows growth sensitivity of a *S. aureus* strain selected using the method outlined in FIGS. 2 & 3 using the murB gene from *S. aureus*. One selected strain that showed growth-inhibited phenotype in the presence of xylose relative to the absence of inducer was characterized in terms of the inducer-dependence of growth attenuation and sensitivity to a panel of antibiotics. The strain showed selective hypersensitivity to antibiotics with mode of action at the cell wall.

In addition to genes corresponding to cell wall biosynthesis, protein synthesis, and DNA synthesis, we have built antisense strains using the method described in FIGS. 2 & 3 to obtain antisense strains in *B. anthracis* for the individual steps in non-mevalonate isoprenoid biosynthesis; for gyrA and gyrB, enzymes involved in DNA replication and the target proteins for the fluoroquinoline antibiotics such as novobiocin, ciprofloxacin, levofloxacin, and trovafloxacin; and for fabF mdfabH, steps in fatty acid biosynthesis. These results further illustrate the general applicability and utility in the method described in FIGS. 2 & 3 as pertaining to the variety of cellular metabolic processes relevant to this process.

Examples 1 & 2 are genetic maps of the regions of the metRS1 and metRS genes that generated xylose-responsive growth inhibitory antisense fragments from B. anthracis and S. aureus. These examples illustrate that the region of the gene and the fragment length producing useful xylose responsive growth inhibitory fragments are efficiently generated using the method described in FIGS. 2 & 3. These examples also illustrate that each gene has characteristic regions and fragment lengths. These fragments are found efficiently using the method described in FIGS. 2 & 3.

Example 3 is a genetic map of the regions of the murB2 gene from B. anthracis that generated xylose-responsive growth inhibitory antisense fragments. This example illustrates how certain genes have regions that are more or less likely to generate useful fragments.

Examples 4 & 5 are genetic maps of the regions of the glmU gene and murA1 gene from B. anthracis that generated xylose-responsive growth inhibitory antisense fragments. These examples illustrate that each gene in the peptidoglycan biosynthesis pathway can be used in the method described in FIGS. 2 & 3. We have similarly generated useful strains for the other steps in the peptidoglycan pathway.

Examples 6, 7, and 8 are genetic maps of the regions of the dxs, dxr-2, and gcpE genes from B. anthracis that generated xylose-responsive growth inhibitory antisense fragments. These examples illustrate that genes from the non-mevalonate isoprenoid biosynthesis pathway can be used in the method described in FIGS. 2 & 3. We have similarly generated useful strains for the other steps in the non-mevalonate isoprenoid biosynthesis pathway.

Example 9 are genetic maps of the regions of the gyrA and gyrB genes from B. anthracis that generated xylose-responsive growth inhibitory antisense fragments. These examples illustrate that genes involved in DNA replication can be used in the method described in FIGS. 2 & 3.

Example 10 is the genetic map of the regions of the fabF gene from B. anthracis that generated xylose-responsive growth inhibitory antisense fragments. This examples illustrates that genes involved in fatty acid biosynthesis can be used in the method described in FIGS. 2 & 3.

Although the invention has been described with reference to the above examples, it will be understood that modifications and variations are encompassed within the spirit and scope of the invention. Accordingly, the invention is limited only by the following claims.

The invention claimed is:

1. A method for generating and selecting drug-sensitizing antisense DNA fragments comprising:

selecting a gene of interest using means other than genomic surveys of antisense-defined proliferation genes, amplification of the gene of interest using genomic DNA as a template, fragmentation of the DNA by sonication or other means;

selecting DNA fragments no longer than 400 base pairs;

ligating the DNA fragments into a suitable expression plasmid with a selectable marker;

transforming the plasmids containing the DNA fragments into the organism from which the gene of interest originated; and selecting clones from transformed cells that show a discernible phenotypic difference of the clone grown in the presence of the inducer relative to the phenotype in the absence of inducer.

2. The method of claim 1, wherein the discernible phenotype is relative sensitivity to a growth inhibiting compound.

3. The method of claim 1, wherein the discernible phenotype is requirement of a nutrient to the growth medium.

4. The method of claim 1, wherein the discernible phenotype is visible morphology such as shape.

5. The method of claim 1, wherein the discernible phenotype is relative sensitivity to osmotic stress.

6. The method of claim 1 wherein the discernible phenotype is colony size.

7. The method of claim 1, wherein the drug is an antibiotic acting through inhibition of DNA biosynthesis.

8. The method of claim 1, wherein the drug is an antibiotic acting through inhibition of RNA biosynthesis.

9. The method of claim 1, wherein the drug is an antibiotic acting through inhibition of protein biosynthesis.

10. The method of claim 1, wherein the drug is an antibiotic acting through inhibition of fatty acid biosynthesis.

11. The method of claim 1, wherein the drug is an antibiotic acting through inhibition of cell wall biosynthesis.

12. The method of claim 1, wherein the drug is an antibiotic acting through inhibition of amino acid biosynthesis.

13. The method of claim 1, wherein the drug is an antibiotic acting through inhibition of nucleotide biosynthesis.

14. The method of claim 1, wherein the drug is an antibiotic acting through inhibition of vitamin biosynthesis.

15. The method of claim 1, wherein the drug is an antibiotic acting through inhibition of isoprenoid biosynthesis.

16. The method of claim 1, wherein the drug is an antibiotic acting through inhibition of co-factor biosynthesis.

17. The method of claim 1, wherein the drug is an antibiotic acting through inhibition of MurB.

18. The method of claim 1, wherein the drug is an antibiotic acting through inhibition of UppS.

19. The method of claim 1, wherein the drug is an antibiotic acting through inhibition of DHFR.

20. The method of claim 1, wherein the drug is a beta-lactam antibiotic.

21. The method of claim 1, wherein the drug is a diaminopyrimidine antibiotic.

22. The method of claim 1, wherein the drug is macrolide antibiotic.

23. The method of claim 1, wherein the drug is daptomycin.

24. The method of claim 1, wherein the drug is a fluoroquinolone antibiotic including ciprofloxacin.

25. The method of claim 1, wherein the drug is a tetracycline.

26. The method of claim 1, wherein the drug is an oxazolidinone.

27. The method of claim 1, wherein the drug is fosfomycin.

28. The method of claim 1, wherein the drug is fosmidomycin.

29. The method of claim 1, wherein the drug is mupirocin.

30. The method of claim 1, wherein the drug is a lipopeptide.

31. The method of claim 1, wherein the drug is a glycopeptide.

32. The method of claim 1, wherein the drug is vancomycin.

33. The method of claim 1, wherein the drug is trimethoprim.

34. The method of claim 1, wherein said antisense-oriented fragment is a fragment of the *Bacillus anthracis* gene murB-2 and is comprised of the sequence specified for SEQ ID:1 Ba-murB2-C1.

35. The method of claim 1, wherein said antisense-oriented fragment is a fragment of the *Bacillus anthracis* gene murB-2 and is comprised of the sequence specified for SEQ ID:2 Ba-murB2-H1.

36. The method of claim 1, wherein said antisense-oriented fragment is a fragment of the *Bacillus anthracis* gene murB-2 and is comprised of the sequence specified for SEQ ID:3 Ba-murB2-D1.

37. The method of claim 1, wherein said antisense-oriented fragment is a fragment of the *Bacillus anthracis* gene murB-2 and is comprised of the sequence specified for SEQ ID:4 Ba-murB2-D2.

38. The method of claim 1, wherein said antisense-oriented fragment is a fragment of the *Bacillus anthracis* gene metS and is comprised of the sequence specified for SEQ ID:5 Ba-metRS1-H1.

39. The method of claim 1, wherein said antisense-oriented fragment is a fragment of the *Bacillus anthracis* gene metS and is comprised of the sequence specified for SEQ ID:6 Ba-metRS1-H2.

40. The method of claim 1, wherein said antisense-oriented fragment is a fragment of the *Bacillus anthracis* gene metS and is comprised of the sequence specified for SEQ ID:7 Ba-metRS1-H6.

41. The method of claim 1, wherein said antisense-oriented fragment is a fragment of the *Bacillus anthracis* gene metS and is comprised of the sequence specified for SEQ ID:8 Ba-metRS1-E4.

42. The method of claim 1, wherein said antisense-oriented fragment is a fragment of the *Bacillus anthracis* gene uppS and is comprised of the sequence specified for SEQ ID:9 Ba-uppS-UG9.

43. The method of claim 1, wherein said antisense-oriented fragment is a fragment of the *Bacillus anthracis* gene uppS and is comprised of the sequence specified for SEQ ID:10 Ba-uppS-UA3.

44. The method of claim 1, wherein said antisense-oriented fragment is a fragment of the *Bacillus anthracis* gene dfrA and is comprised of the sequence specified for SEQ ID:11 Ba-dfrA-2G1.

45. The method of claim 1, wherein said antisense-oriented fragment is a fragment of the *Bacillus anthracis* gene dfrA and is comprised of the sequence specified for SEQ ID:12 Ba-dfrA-2G6.

46. The method of claim 1, wherein said antisense-oriented fragment is a fragment of the *Staphylococcus aureus* gene murB and is comprised of the sequence specified for SEQ ID:13 Sa-murB-E9.

47. The method of claim 1, wherein said antisense-oriented fragment is a fragment of the *Staphylococcus aureus* gene murB and is comprised of the sequence specified for SEQ ID:14 Sa-murB-F7.

48. The method of claim 1, wherein said antisense-oriented fragment is a fragment of the *Staphylococcus aureus* gene murB and is comprised of the sequence specified for SEQ ID:15 Sa-murB-B9.

* * * * *